United States Patent [19]

Christensen et al.

[11] 4,383,946
[45] May 17, 1983

[54] PROCESS FOR THE PREPARATION OF 1-CARBAPENEMS AND INTERMEDIATES VIA SILYL-SUBSTITUTED DITHIOACETALS

[75] Inventors: Burton G. Christensen, Scotch Plains; Ronald W. Ratcliffe, Matawan; Thomas N. Salzmann, North Plainfield, all of N.J.

[73] Assignee: Merck & Co., Inc., Rahway, N.J.

[21] Appl. No.: 303,459

[22] Filed: Sep. 18, 1981

Related U.S. Application Data

[63] Continuation of Ser. No. 134,397, Mar. 27, 1980.

[51] Int. Cl.$^3$ .......................................... C07D 487/04
[52] U.S. Cl. ....................... 260/245.2 T; 260/239 A; 424/274; 544/144; 544/316; 544/373; 546/157; 546/272
[58] Field of Search ................................. 260/245.2 T

[56] References Cited

U.S. PATENT DOCUMENTS 4,273,709  6/1981  Christensen et al. ........ 260/245.2 T
4,282,148  8/1981  Liu et al. ..................... 260/245.2 T
4,287,123  9/1981  Liu et al. ..................... 260/245.2 T Primary Examiner—Mary C. Lee
Attorney, Agent, or Firm—James A. Arno; Hesna J. Pfeiffer

[57] ABSTRACT

Disclosed is a process for the total synthesis of 1-carbapenem antibiotics (I) from L-aspartic acid via central intermediates II and III:

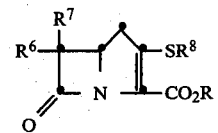

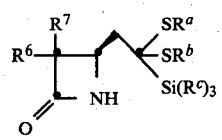

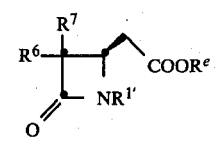

wherein R is hydrogen, a pharmaceutically acceptable ester moiety or salt cation, or a readily removable blocking group; $R^6$, $R^7$ and $R^8$ are, inter alia, independently selected from the group consisting of hydrogen, alkyl, alkenyl, aryl and aralkyl; $R^{1'}$ and $R^e$ are hydrogen, or a readily removable protecting group; $R^a$, $R^b$ and $R^c$ are selected from alkyl, aryl or aralkyl.

1 Claim, No Drawings

PROCESS FOR THE PREPARATION OF 1-CARBAPENEMS AND INTERMEDIATES VIA SILYL-SUBSTITUTED DITHIOACETALS

This is a continuation of application Ser. No. 134,397 filed Mar. 27, 1980.

BACKGROUND OF THE INVENTION

This invention relates to the total synthesis of certain 1-carbapenems and their pharmaceutically acceptable salt, ester and amide derivatives which are useful as antibiotics. Such compounds may generically be represented by the following structural formula:

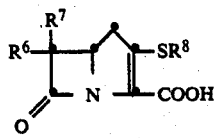
I wherein $R^6$, $R^7$, and $R^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl; wherein the substituent or substituents relative to the above-named radicals are selected from the group consisting of:

—X' halo (chloro, bromo, fluoro)
—OH hydroxy
—OR¹ alkoxy, aryloxy

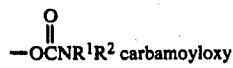

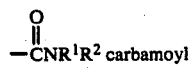

—NR¹R² amino

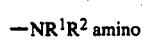

—SO₂NR¹R² sulfonamido

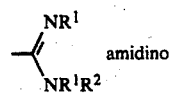

—CO₂H carboxy
—CO₂R¹ carboxylate

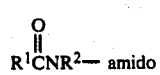

—SH mercapto

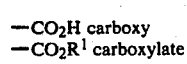

—CN cyano
—N₃ azido wherein, relative to the above listed substituents on $R^6$, $R^7$, and $R^8$, the groups $R^1$ and $R^2$ are independently selected from: hydrogen, alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl and wherein the hetero atom or atoms in the above-named heterocyclic moieties are selected from the group consisting of 1-4 oxygen, nitrogen or sulphur atoms and wherein the alkyl moieties associated with said heterocyclic moieties have 1-6 carbon atoms.

This invention also relates to the carboxyl derivatives of I which are antibiotics and which may be represented by the following generic structure (I):

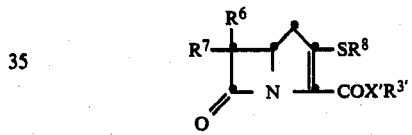
I wherein X' is oxygen, sulphur or NR' (R'=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below.

Starting from L-aspartic acid, the synthesis proceeds via intermediates II, III, IV and V:

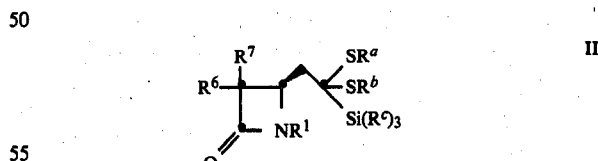
II

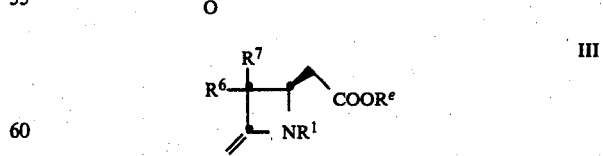
III

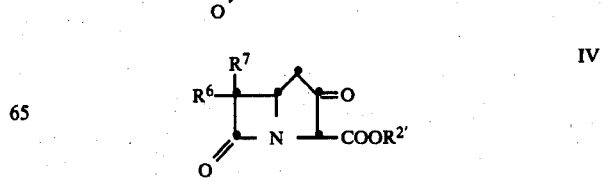
IV

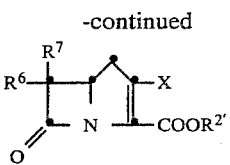

wherein $R^6$ and $R^7$ are as previously defined; X is a conventional leaving group and $R^{2'}$ is hydrogen, a pharmaceutically acceptable ester moiety or a conventional, readily removable protecting group or salt cation. For intermediates IV, $R^{2'}$ is as defined but preferably is an ester moiety defined under $R^{2'}$; $R^{1'}$ is hydrogen or a readily removable protecting group such as a triorganosilyl group; $R^a$ and $R^b$ are selected from alkyl, aryl or aralkyl such as methyl, ethyl, benzyl, ethoxybenzyl, trityl, phenyl, for example; additionally, $R^a$ and $R^b$ may be joined together, to form a radical such as —$(CH_2)_3$— to bridge the two sulphur atoms; $R^c$ is alkyl, aralkyl or aryl, such as methyl, ethyl or phenyl, for example. The details of the total synthesis are given below.

The final compounds prepared by the process of this invention are disclosed and claimed in the following co-pending, commonly assigned U.S. patent application Ser. No. 843,375 filed Oct. 19, 1977; now abandoned; U.S. patent application Ser. No. 933,681 filed Aug. 17, 1978; now abandoned; U.S. patent application Ser. No. 31,694 filed Apr. 19, 1979 now abandoned, and in concurrently filed U.S. patent application Ser. Nos. 134,604, 129,851, 134,381, all now abandoned. To the extent that the foregoing U.S. Patent Applications describe the antibiotic utility of final compounds I and to the extent that they define substituents $R^6$, $R^7$, $R^8$, $R'$, $X'$ and $R^{3'}$ they are hereby incorporated by reference.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The process of the present invention may conveniently be summarized by the following reaction diagram:

DIAGRAM I

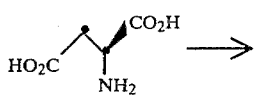

1

-continued
DIAGRAM I

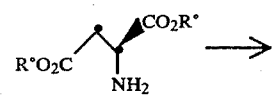

2

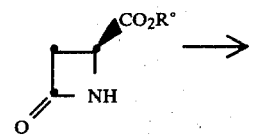

3

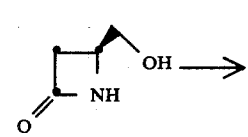

4

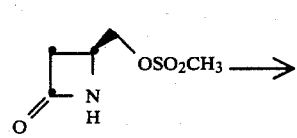

5

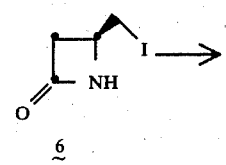

6

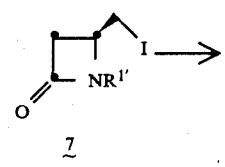

7

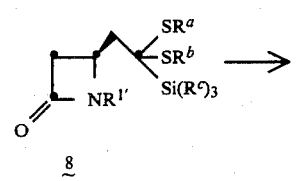

8

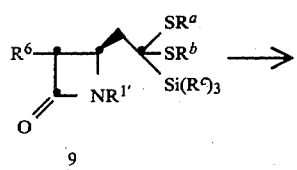

9

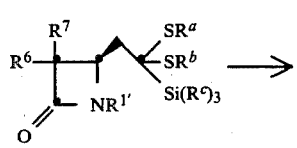

10

-continued
DIAGRAM I

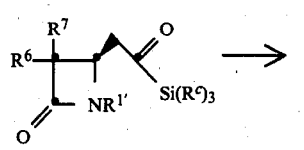

11

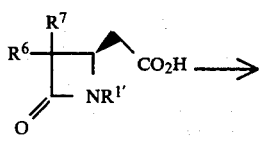

12

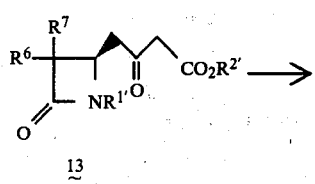

13

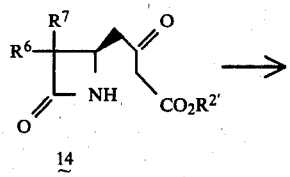

14

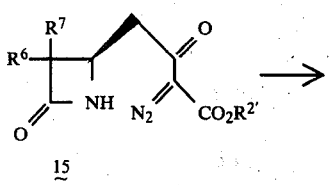

15

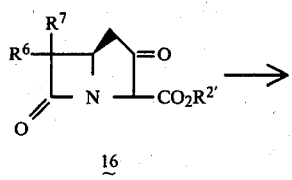

16

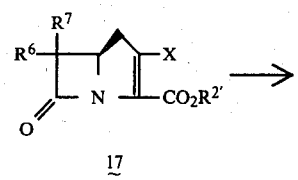

17

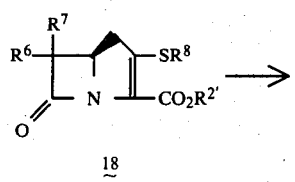

18

-continued
DIAGRAM I

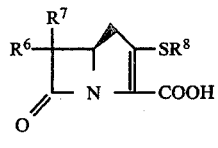

I

In words relative to the above diagram, L-aspartic acid 1 is esterified according to well known procedures. Typically 1 in a solvent such as benzene, toluene, chloroform or the like is treated with an esterifying agent such as benzyl alcohol, methanol, ethanol, isopropanol, or the like in the presence of p-toluene sulfonic acid, HCl, HBr, or the like at a temperature of from 0° to 110° C. for from 1 to 24 hours to achieve the desired establishment and hence protection of the carboxyl functions. Thus, R° is any convenient carboxyl protecting group such as benzyl, methyl, ethyl, isopropyl, or the like. The resulting species 2 in a solvent such as ether, THF, DME or the like is treated with trimethylchlorosilane, or the like followed by treatment with EtMgBr, MeMgI, φMgBr, t-BuMgCl, or the like at a temperature of from −40° to 50° C. for from 1 to 72 hours to provide azetidinone 3. Reduction of species 3 with a reducing agent such as NaBH₄, or the like in a solvent such as methanol, ethanol, isopropanol or the like at a temperature of from −10° to 40° C. for from 1 to 6 hours provides 4. (For purposes here, the symbols: Et, Me, φ, iPr, and t-Bu stand for: ethyl, methyl, phenyl, isopropyl, and tert-butyl, respectively.)

Treatment of 4 in a solvent such as methylene chloride, CHCl₃ or the like with methane sulfonyl chloride, methane sulfonic anhydride or the like in the presence of a base such as Et₃N, iPr₂NEt, or the like followed by treatment with a stoichiometric to 5-fold excess of sodium iodide in acetone yields 6 via 5.

The transformation 6→7 establishes the protecting group R¹' which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R¹' is established by treating 6 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° to 25° C. for from 0.5 to 24 hours in the presence of a base such as triethylamine, diisopropylethylamine or imidazole.

The transformation 7→8 is accomplished by treating 7 in a solvent such as tetrahydrofuran, dimethoxyethane, diethylether or the like with a carbanion generically represented by the following structure:

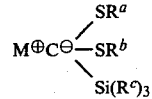

wherein M is a metal cation such as lithium, potassium copper or magnesium, for example, and Rᵃ, Rᵇ and Rᶜ are as defined above at a temperature of from −100° to 0° C. and from 0.5 to 4 hours.

Typically, the carbanion reagent is prepared prior to addition of substrate 7 on treatment of the diorganothiomonoorganosilylmethane with a strong base such as n-butyllithium, t-butyllithium, phenyllithium, lithium diisopropylamide(LDA) or the like.

Resulting intermediate 8 can be mono-, or dialkylated at ring position 3. Alkylation of 8 provides 9. Typically, 8 is treated with a strong base such as lithium diisopropylamide, lithium 2,2,6,6-tetramethylpiperidide, potassium hydride, lithium hexamethyldisilazane, phenyllithium or the like in a solvent such as tetrahydrofuran(THF), hexamethylphosphoramide, ether, dimethoxyethane, and the like at a temperature of from −80° C. to 0° C. whereupon the alkylating agent of choice, $R^6X°$ is added ($X°$ is chloro, iodo or bromo); alternatively the alkylating agent may be $R^6$-tosylate, $R^6$-mesylate or an aldehyde or ketone such as acetaldehyde to provide monoalkylated species 9. When desired, dialkylated species 10 may be obtained from 9 by repeating the alkylating procedures 8→9.

The eventual 6-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing, $R^6$ and $R^7$.

The following list is representative of useful alkylating agents for establishing $R^6$ and $R^7$, according to the above scheme: 8→9→10 (this will be referred to as Scheme I, to be distinguished from Scheme II, below, which involves acylation):

Alkylating Agents

CH₃CHO
φCH₂CHO    φ = phenyl
φCH₂CH₂CHO
CH₂O
CH₃I
φCH₂Br
CH₃COCH₃

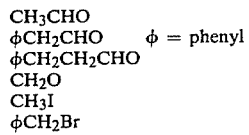

CH₃OCH₂CHO
CH₃CH₂I
(CH₃)₂CHI
N₃CH₂CHO
Me₂NCH₂CHO
RO₂CCH₂Br    R = CH₃, benzyl, p-nitrobenzyl
CF₃CF₂CHO
RO₂CCH₂CHO    R = CH₃, benzyl, p-nitrobenzyl
CH₃CH(CH₃)CHO,
CH₃(CH₃)CHCH₂CHO,
CH₃CH₂CHO,
CH₂=CH—CHO

CF₃CHO,

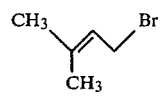

-continued
Alkylating Agents

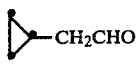

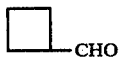

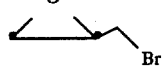

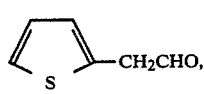

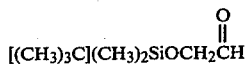

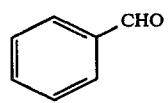

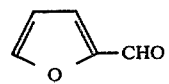

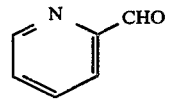

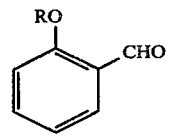    R = protecting group

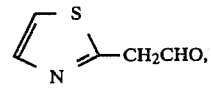

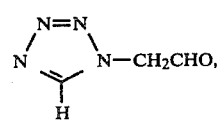

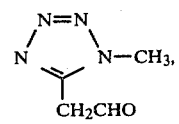

-continued
Alkylating Agents

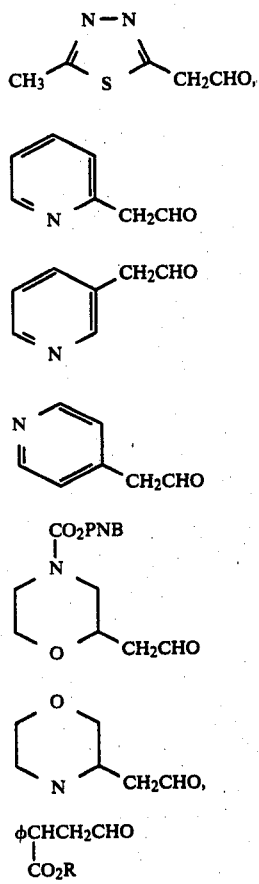

φCHCH₂CHO
|
CO₂R

R is removable carboxyl protecting group, such as benzyl.

As mentioned above, the 6-substituents may also be established by acylation. Utilization of such acylating agents may be demonstrated in the following manner with regard to a preferred starting, or intermediate material 10:

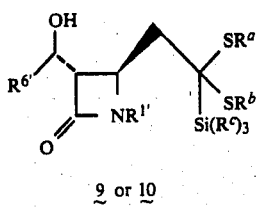

9 or 10 wherein R⁷ and R¹' are as defined above. R⁶' is defined relative to the definition of R⁶ and in that sense is the balance of the previously identified group R⁶. In other words, for purposes of this definition R⁶'CH(OH-)—=R⁶. An especially preferred material 10 is when R⁷ is hydrogen and R⁶' is methyl.

Such preferred starting materials are described in the following co-pending, commonly assigned U.S. patent application Ser. No. 59,844 filed July 23, 1979 which is incorporated herein by reference. Basically, such 1'-hydroxy R⁶' species 10 are prepared according to the following scheme:

SCHEME II

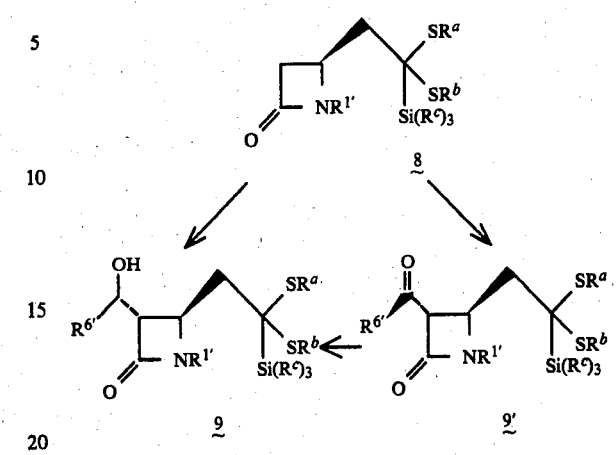

The alkylation 8→9, Scheme II, is accomplished as previously described, by treating 8 in a solvent such as tetrahydrofuran, dimethoxyethane, diethylether, hexamethylphosphoramide, at a temperature of from −100° to −20° C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde. This reaction gives a mixture of isomers from which the desired trans-R form 9 (or 10) can be conveniently separated by chromatography or crystallization.

Intermediate 8 may proceed directly to 9 as indicated above, or it may take the circuitous path via 9'. The direct acylation, to 9' is accomplished by treating 8 with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to −20° C. with an acylating agent such as N-acyl imidazole or the like. Addition of the 8 plus base mixture to the acylating agent is preferred.

Representative acylating agents for this scheme 8→9'→9 are listed below.

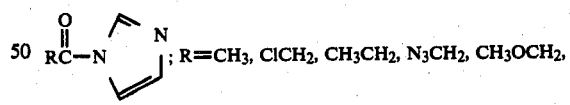

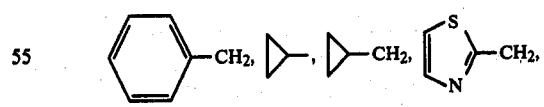

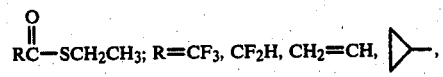

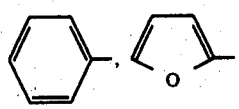

Further with respect to Scheme II, the reduction 9'→9 is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethylether, tetrahydrofuran, toluene or the like at a temperature of from −78° to 25° C. The reaction can conveniently be conducted in the presence of an added complexing salt such as potassium iodide, magnesium bromide or the like.

In a similar manner, unresolved 9 (cis and trans) may be oxidized to 9' for reduction to 9 as indicated above:

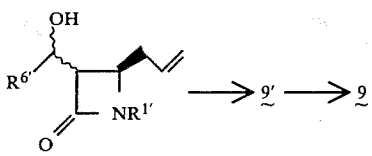

The oxidation is accomplished with an oxidizing agent such as dipyridine chromium (VI) oxide, trifluoroacetic anhydride-dimethylsulfoxide-triethylamine, pyridinium dichromate, acetic anhydride-dimethylsulfoxide in a solvent such as methylene chloride, acetonitrile, or the like at a temperature of from −78° to 25° C. for from 5 minutes to 5 hours.

Now return to the main course of reaction, DIAGRAM I, and the transformation 10→11. The transformation is accomplished by treating 10 in a solvent such as methanol, ethanol, isopropanol, water or the like at a temperature of from 0° to 80° C. with a Lewis acid such as mercuric chloride, silver tetrafluoroborate, thallium trinitrate or the like.

The oxidation 11→12 is preferably achieved with a 1.0 to 5.0 fold excess of an oxidizing agent such as m-chloroperbenzoic acid, peracetic acid, hydrogen peroxide, pertrifluorocacetic acid, or the like, in a solvent such as chloroform, carbontetrachloride, chlorobenzene, or the like, at a temperature of from 25° C. to 130° C. for from 0.5 to 24 hours.

The addition 12→13 is accomplished by treating 12 with 1,1'-carbonyldimidazole, or the like, in a solvent such as tetrahydrofuran, dimethoxyethane, DMF, or the like, at a temperature of from 0° to 50° C., followed by the addition of 0.5 to 3.0 equivalents of ($R^{2'}O_2CCH_2CO_2)_2Mg$, at a temperature of from 0 to 50° C. for from 1 to 48 hours. $R^{2'}$ is a readily removable carboxyl protecting group such as p-nitrobenzyl, benzyl, or the like. It should also be noted that $R^{2'}$ may be a pharmaceutically acceptable ester moiety; such ester groups are representatively mentioned below. (DMF is dimethylformamide.)

Removal of protecting group $R^{1'}$ (13→14) may be accomplished by a variety of known procedures such as hydrolysis or hydrogenation. When $R^{1'}$ is a triorganosilyl group (for example, [$(CH_3)_3C$]($CH_3)_2Si$—) removal is typically accomplished by acidic aqueous hydrolysis of 13 in a solvent such as methanol, ethanol, tetrahydrofuran, dioxane, DMF, or the like in the presence of an acid such as hydrochloric, sulfuric, acetic or the like at a temperature of from 0° to 100° C. for from 2 to 18 hours.

It should be noted that an otherwise identical deblocking can occur at level 10, 11, or 12. Thus, when $R^{1'}$=H, the chain elongation can proceed directly from 12 to 14.

The diazo species 15 is prepared from 14 by treating 14 in a solvent such as $CH_3CN$, $CH_2Cl_2$, THF, or the like, with an azide such as p-carboxybenzenesulfonylazide, toluenesulfonylazide, methanesulfonylazide, or the like, in the presence of a base such as triethylamine, pyridine, $(C_2H_5)_2NH$, or the like, for from 1 to 50 hours at 0°-25° C. (THF is tetrahydrofuran.)

Cyclization (15→16) is a-complished by treating 15 in a solvent such as benzene, toluene, THF, or the like, at a temperature of from 50°-110° C. for from 1-5 hours in the presence of a catalyst such as bis (acetylacetonato)-Cu(II) [Cu(acac)$_2$], CuSO$_4$, Cu powder, Rh(OAc)$_2$, or Pd(OAC)$_2$. Alternatively, the cyclization may be accomplished by irradiating 15 through a pyrex filter (a wave length greater than 300 nm) in a solvent such as benzene, CCl$_4$, diethylether, or the like, at a temperature of from 0°–25° C. for from 0.5 to 2 hours. ["OAc"=acetate.]

Establishment of leaving group X (16→17) is accomplished by acylating the keto ester 16 with an acylating agent R°X such as p-toluenesulfonic acid anhydride, p-nitrophenylsulfonic acid anhydride, 2,4,6-triisopropylphenylsulfonic acid anhydride, methanesulfonic acid anhydride, trifluoromethane sulfonic acid anhydride, diphenyl chlorophosphate, toluenesulfonyl chloride, p-bromophenylsulfonyl chloride, or the like; wherein x is the corresponding leaving group such as toluene sulfonyloxy, p-nitrophenylsulfonyloxy, diphenylphosphoryl, and other leaving groups which are established by conventional procedures and are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.1 to 5 hours. The leaving group X of intermediate 17 can also be halogen. The halogen leaving group is established by treating 17 with a halogenating agent such as $\phi_3PCl_2$, $\phi_3PBr_2$, $(\phi O)_3PBr_2$, oxalyl chloride or the like in a solvent such as $CH_2Cl_2$, $CH_3CN$, THF, or the like in the presence of a base such as diisopropylethylamine, triethylamine, or 4-dimethylaminopyridine or the like. [$\phi$=phenyl.]

The reaction 17→18 is accomplished by treating 17 in a solvent such as dioxane, dimethylformamide, dimethylsulfoxide, acetonitrile, hexamethylphosphoramide, or the like in the presence of an approximately equivalent to excess of the mercaptan reagent. HSR$^8$, wherein R$^8$ is as defined above, in the presence of a base such as sodium hydrogen carbonate, potassium carbonate, triethylamine, diisopropylethylamine, or the like at a temperature of from −40° to 25° C. for from 1 to 72 hours. When R$^8$ is substituted by a primary or secondary amino group, for example —$CH_2CH_2NH_2$, the mercaptan reagent may be represented as HSCH$_2$CH$_2$NHR°, for example; wherein R° is a readily removable N-protecting group such as p-nitrobenzyloxycarbonyl, (—CO$_2$PNB), o-nitrobenzyloxycarbonyl, or the like. The specifically illustrated mercaptan reagent, HSCH$_2$CH$_2$NHR°, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours. The foregoing mercaptan reagent, HSR$^8$, and means for its protection, is simply illustrative. The class of suitable HSR⁸ reagents is representatively described below and in the Examples.

The final deblocking step 18→I is accomplished by conventional procedures such as solvolysis or hydrogenation. Typically 18 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.25 to 4 hours to provide I. Photolysis, when R²′ is a group such as o-nitrobenzyl, for example, may also be used for deblocking.

Introduction of the Thia Side Chain

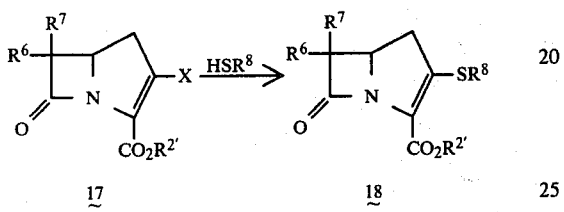

Relative to the foregoing description of the invention, suitable reagents HSR⁸ utilized in the transformation 17→18 are listed below. The list is arranged according to structural and functional characteristics of the thia side chain —SR⁸; annotation is provided where necessary. The thia side chain of choice is derived from the corresponding mercaptan reagent HSR⁸. When the mercaptan contains a functional group which might interfere with the intended course of reaction, the offending group is covered. For example, when a basic nitrogen group is encountered (—NHR or —NH₂, for example) it is usually protected by acylation (e.g., —CO₂PNB) and when a carboxyl group (—CO₂H) is present, it is usually protected by esterification (e.g., PNB ester). Such protection also facilitates in the purification of products 18 by chromatographic means. (PNB is p-nitrobenzyl).

(1.) Aliphatic Mercaptans: HSR⁸ wherein R⁸ is 1–10 carbon alkyl, cycloalkyl, alkenyl, cycloalkenyl, or alkynyl; R⁸ may be branched or unbranched, Examples

HSCH₃
HSCH₂CH₃
HSCH₂CH₂CH₃
HSCH(CH₃)₂
HS(CH₂)₃CH₃

HS—CH—CH₂CH₃
   |
  CH₃

HSCH₂CH(CH₃)₂

CH₃
    |
HS—C—CH₃
    |
    CH₃

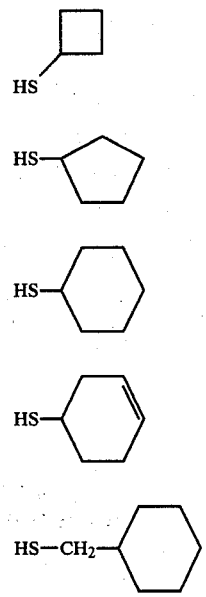

HS—CH₂—CH=CH₂
HS—CH₂—CH=C(CH₃)₂
HS—CH₂—C≡CH
HS—CH₂—C≡C—CH₃

(2.) Substituted Aliphatic Mercaptans:

HSR⁸ wherein R⁸ is a 1–10 carbon branched or unbranched alkyl, cycloalkyl, alkenyl, cycloalkenyl or alkynyl group substituted by one or more halo, $$OH, OR^1, O\overset{O}{\underset{\|}{C}}R^1, O\overset{O}{\underset{\|}{C}}NH_2, O\overset{O}{\underset{\|}{C}}NR^1R^2, NH_2, NHR^1,$$

$$NR^1R^2, \overset{O}{\underset{\|}{C}}R^1, CO_2H, CO_2R^1, CONH_2, CONHR^1, CONR^1R^2,$$

$$CN, SR^1, \overset{O}{\underset{\|}{S}}R^1, SO_2R^1, SO_2NH_2, SO_2NHR^1, SO_2NR^1R^2, NH\overset{O}{\underset{\|}{C}}R^1,$$

$$NH\overset{O}{\underset{\|}{C}}NH_2, NH\overset{O}{\underset{\|}{C}}NHR^1, NH\overset{O}{\underset{\|}{C}}NR^1R^2, NH\overset{O}{\underset{\|}{C}}OR^1, \overset{NH}{\underset{\|}{C}}NH_2, \overset{NR^1}{\underset{\|}{C}}NHR^2,$$

wherein R¹ and R² are as previously defined relative to substituents on R⁸. Preferred substituents are basic nitrogen containing groups.

EXAMPLES $$HS(CH_2)_nOR^1 \quad n = 2-4, R^1 = H, \overset{O}{\underset{\|}{C}}CH_3, CH_3$$

$$HS(CH_2)_n\overset{O}{\underset{\|}{C}}XR \quad n = 1-3, X = O, NH, NR^1 \quad R^1 = H, CH_3$$

HS(CH₂)ₙNH₂    n = 2–4
HS(CH₂)ₙNHR¹    n = 2–4, R¹ = CH₃, CH₂CH₃, $$CH_2CH_2CH_3, \overset{O}{\underset{\|}{C}}CH_3$$

HS(CH₂)ₙNR¹R²    n = 2–4, R¹/R² = CH₃, CH₂CH₃

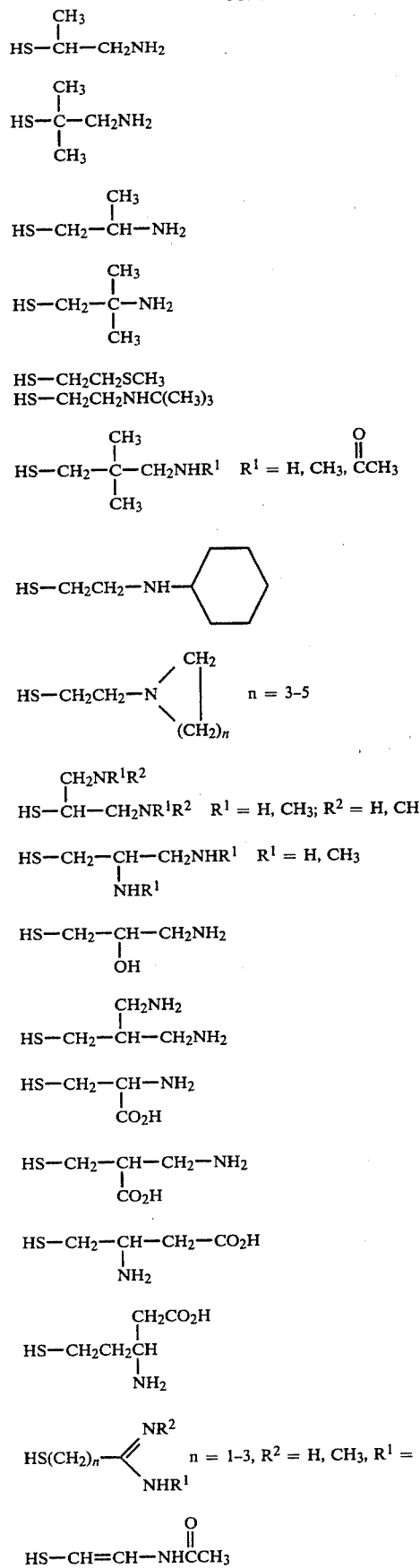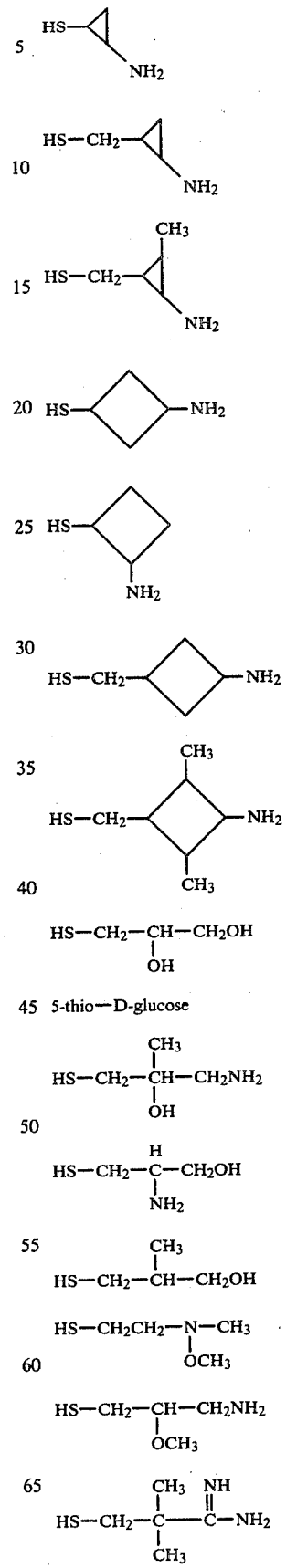

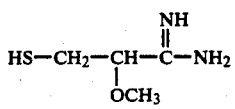
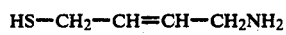
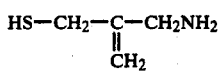
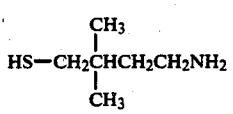
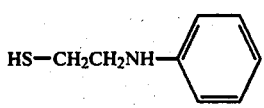
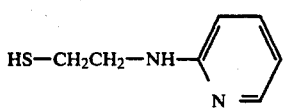
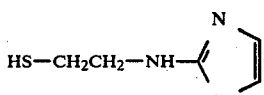
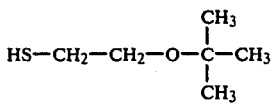

(3) Aryl Mercaptans: $HSR^8$ wherein $R^8$ is phenyl or substituted phenyl. The substituents are independently selected from those previously defined for $R^8$. Especially preferred substituents include alkyl, halo, hydroxy, alkoxy, acyloxy, acyl, carboxy, mercapto, sulfinyl, sulfonyl, amino, substituted amino, aminoalkyl, substituted aminoalkyl, amido, and ureido.

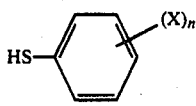

n = 1, 2 or 3, $X = F, Cl, Br, OH, OR, OCR^1, NH_2,$ $NHR^1, NR^1R^2, CH_2NH_2, CH_2NR^1R^2, CO_2H,$
$CO_2R^1, COR^1, CONH_2, CONR^1R^2, R^1CONH,$ $R^1NHCONH, SR^1, SR^1, SO_2R^1, CH_3, CF_3;$ $R^1$ and $R^2$ are as previously defined under $R^8$.

Examples

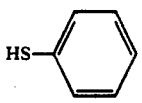

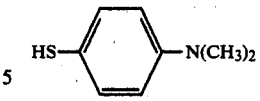
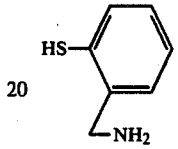
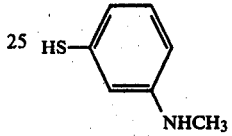
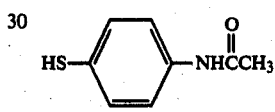
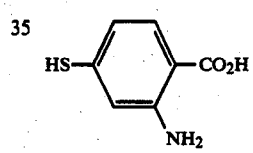

(4) Heteroaryl Mercaptans: $HSR^8$ wherein $R^8$ is a substituted or unsubstituted heteroaryl group containing 1–4 O, N or S atoms. Typical substituents include those mentioned above under "Aryl Mercaptans".

EXAMPLES

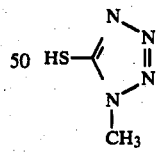
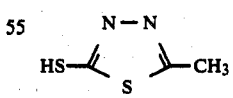
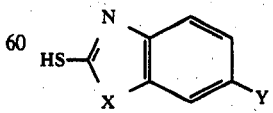

X = N,O  Y = H
X = S    Y = H, Cl, $OCH_2CH_3$

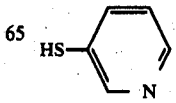

-continued

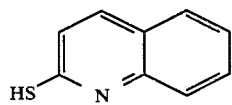

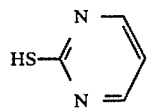

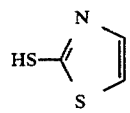

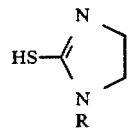  R = H, CH₃

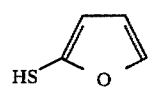

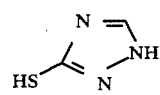

  X = NH, S

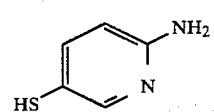

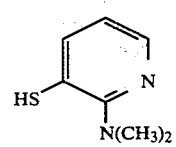

(5) Arylaliphatic Mercaptans: HSR⁸ where R⁸ is a 1-6 carbon branched or unbranched alkyl, cycloalkyl, alkenyl, or alkynyl group substituted by a phenyl or substituted phenyl group. Typical phenyl substituents include those mentioned under "Aryl Mercaptans".

EXAMPLES

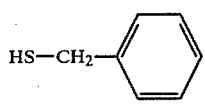

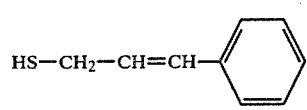

-continued

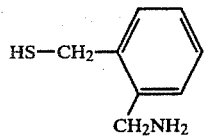

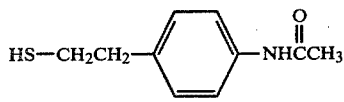

(6) Heteroarylaliphatic and Heterocyclicaliphatic Mercaptans

HSR⁸ wherein R⁸ is a 1-6 carbon branched or unbranched alkyl, cycloalkyl, alkenyl, or alkynyl group substituted by a heteroaryl or heterocyclic group containing 1-4, O, N, or S atoms. The heteroaryl or heterocyclic group is unsubstituted or substituted by those substituents mentioned under "Aryl Mercaptans", (No.3, above).

EXAMPLES

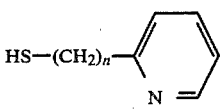

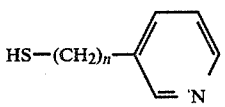

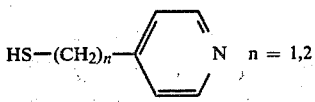  n = 1,2

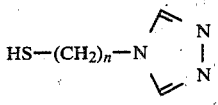

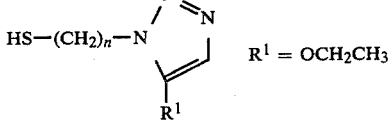  R¹ = OCH₂CH₃

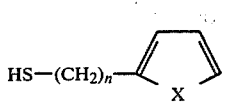

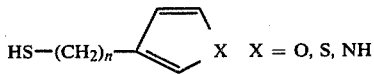  X  X = O, S, NH

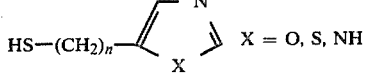  X = O, S, NH

-continued

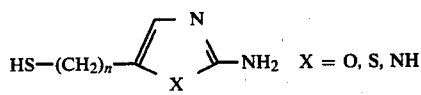 X = O, S, NH

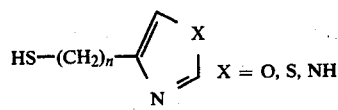 X = O, S, NH

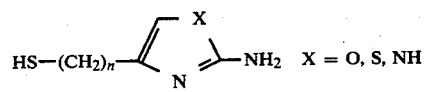 X = O, S, NH

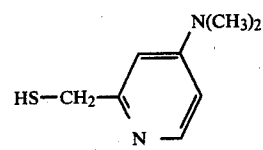

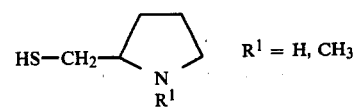 $R^1$ = H, CH$_3$

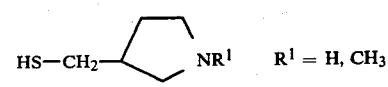 $R^1$ = H, CH$_3$

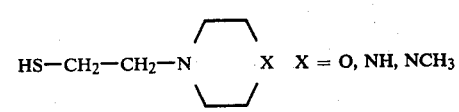 X = O, NH, NCH$_3$

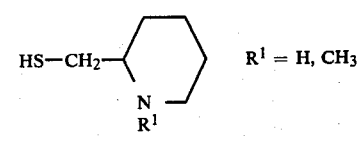 $R^1$ = H, CH$_3$

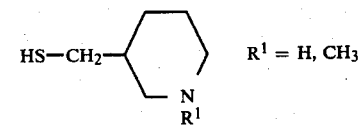 $R^1$ = H, CH$_3$

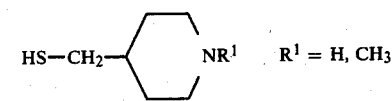 $R^1$ = H, CH$_3$

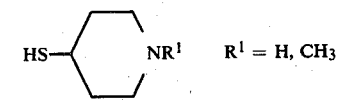 $R^1$ = H, CH$_3$

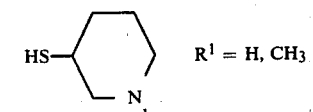 $R^1$ = H, CH$_3$

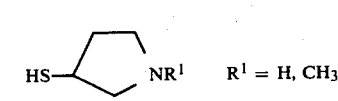 $R^1$ = H, CH$_3$

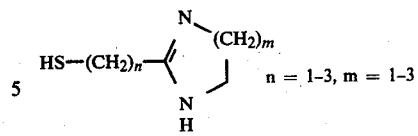 n = 1-3, m = 1-3

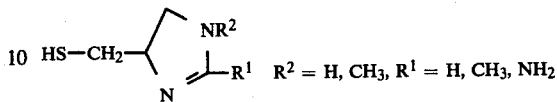 $R^2$ = H, CH$_3$, $R^1$ = H, CH$_3$, NH$_2$

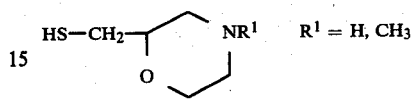 $R^1$ = H, CH$_3$

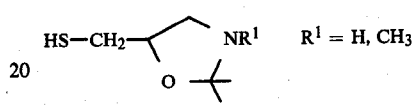 $R^1$ = H, CH$_3$ (7) Alkyl-Heteroatom-Alkyl Mercaptans, HSR$^8$
Wherein R$^8$ is $$-(CH_2)_n X(CH_2)_m R^9$$

wherein n=2 to 4, m=2 to 4; X is NR°, O or S; and wherein R° is

H, CH$_3$, CH$_2$CH$_3$, CH$_2$CH$_2$OH, or CH$_2$CH$_2$NH$_2$ and

R$^9$ is OH, NH$_2$, NHCH$_3$, N(CH$_3$)$_2$, OCCH$_3$, NHCCH$_3$.
$$\qquad\qquad\qquad\qquad\qquad\;\;\; \overset{\|}{O} \quad\;\; \overset{\|}{O}$$

Note, in the above representation, the methylene carbons may be branched; for example:

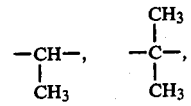

and the like.
The following HSR$^8$ are representative of this class:

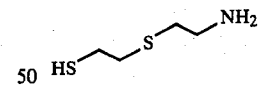 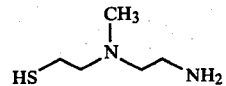

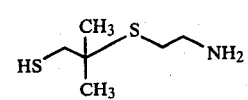 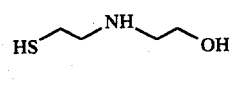

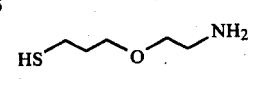 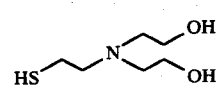

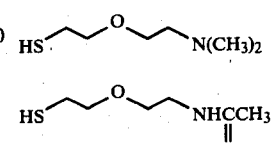

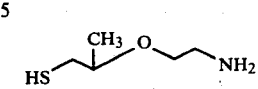

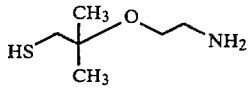

As noted above, the compounds of the present invention may also generally be represented by the following structural formula:

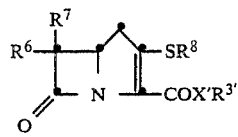

wherein X' is oxygen, sulfur or NR' (R' is a hydrogen or loweralkyl having from 1 to 6 carbon atoms); and $R^{3'}$ is hydrogen, or, inter alia, is representatively selected to provide the pharmaceutically acceptable salt, ester anhydride ($R^{3'}$ is acyl) and amide moieties known in the bicyclic β-lactam antibiotic art; $R^{3'}$ may also be a readily removable blocking group.

Identification of the Radical —COX'R$^{3'}$

In the generic representation of the compounds of the present invention (I, above), the radical represented by —COX'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and nuclear analogues thereof.

Suitable blocking esters ($R^{3'}$, X'=O) include those selected from the following list which is representative:

(i) $R^{3'}$=CR$^a$R$^b$C$^c$ wherein at least one of R$^a$, R$^b$ and R$^c$ is an electron-donor, e.g., p-methoxyphenyl. The remaining R$^a$, R$^b$ and R$^c$ groups may be hydrogen or organic substituting groups. Suitable ester groups of this type include p-methoxybenzyloxycarbonyl.

(ii) $R^{3'}$=CR$^a$R$^b$R$^c$ wherein at least one of R$^a$, R$^b$ and R$^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}$=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: R$^4$$_3$SiX' wherein X' is a halogen such as chloro or bromo and R$^4$ is alkyl, e.g., methyl, ethyl, t-butyl.

Pharmaceutically acceptable carboxyl derivatives of the present invention are those derived by reacting I with alcohols, acylating reagents and the like. For example, esters and amides of interest are the above-listed starting materials and final products having the —COX'R$^{3'}$ group at the 3-position; wherein X' is oxygen, sulfur or NR' (R' is H or R$^{3'}$), and $R^{3'}$ is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl- and nitro- substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

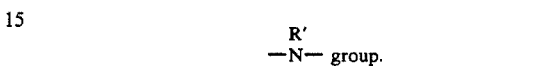

Representative of such amides are those wherein R' is selected from the group consisting of hydrogen and lower alkyl such as methyl and ethyl.

The most preferred —COX'R$^{3'}$ radicals of the present invention are those wherein (relative to Structure I above), X' is oxygen and $R^{3'}$ is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various gram-positive and gram-negative bacteria and accordingly find utility in human and veterinary medicine. Representative pathogens which are sensitive to antibiotics I include: *Staphyloccus aureus, Escherichia coli, Klebsiella pneumoniae, Bacillus subtilis, Salmonella typhosa,* Psuedomonas and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above schematic reaction diagram for the total synthesis of the defined carbapenem antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

Preparation of 4(S)-4-Iodomethylazetidin-2-one

STEP A

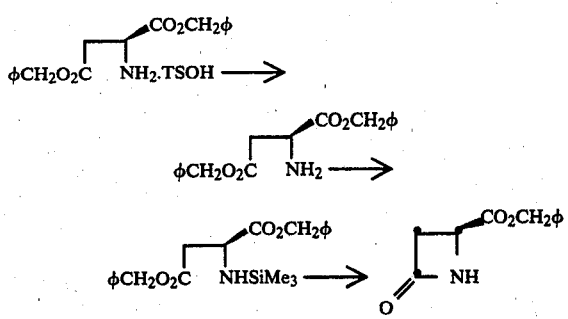

Benzyl (S)-azetidin-2-one-4-carboxylate

To a 1000 ml separatory funnel are added dibenzyl (S)-aspartate p-toluenesulfonic acid salt (48.6 g, 0.1 mole), ice-cold diethyl ether (300 ml), ice-cold water (100 ml), and ice-cold saturated aqueous potassium carbonate (50 ml). The mixture is shaken vigorously and the layers are separated. The aqueous portion is extracted with more cold diethyl ether (2×100 ml). The combined ether solution is washed with brine, dried with magnesium sulfate, and evaporated under vacuum to provide dibenzyl (S)-aspartate (31.4 g, 0.1 mole) as a colorless liquid.

The dibenzyl (S)-aspartate in anhydrous diethyl ether (200 ml) is cooled in an ice-bath under a nitrogen atmosphere. Trimethylchlorosilane (12.7 ml, 0.1 mole) is added to the stirred solution to give a white precipitate. Triethylamine (14.0 ml, 0.1 mole) is then added to the mixture. The cooling bath is removed and the mixture is stirred at room temperature (22°–25° C.) for 2 hrs. The mixture is then filtered directly into a 3-neck, 1.0 liter, round bottom flask fitted with a sintered glass funnel, magnetic stirrer, and a vacuum-nitrogen inlet. This operation is carried out under a blanket of nitrogen, care being taken to exclude atmospheric moisture. The sintered glass funnel is replaced by a stopper and the ether is evaporated under vacuum with stirring to provide dibenzyl (S)-N-trimethylsilylaspartate (35.5 g, 0.092 mole) as a slightly hazy oil.

Anhydrous diethyl ether (250 ml) is added to the flask containing the silyl derivative and the magnetic stirrer is replaced by a mechanical stirrer. The resulting solution is stirred under a nitrogen atmosphere with ice-bath cooling. Ethereal ethyl magnesium bromide (34 ml of a 2.94 M solution, 0.1 mole) is added dropwise over 40 min. to give a cream colored, stirable precipitate. The cooling bath is removed and the mixture is stirred at room temperature. After 1.5 hrs, a viscous gum forms. The mixture is allowed to stand overnight at room temperature. The mixture is then cooled in an ice-methanol bath while ammonium chloride saturated 2 N hydrochloric acid (100 ml) is added slowly with stirring. The resulting mixture is diluted with ethyl acetate (100 ml) and water (100 ml) and the layers are separated. The aqueous portion is extracted with more ethyl acetate (3×100 ml). The combined organic solution is washed with water (200 ml), 5% aqueous sodium bicarbonate solution (100 ml), water (100 ml), and brine, dried with magnesium sulfate, and filtered. Evaporation of the solvent under vacuum gives an orange oil interspersed with a fine, granular precipitate (25.3 g). This material is dissolved in warm chloroform (75 ml), diluted with petroleum ether (125 ml), seeded, scratched, and cooled in an ice-bath. The precipitate is collected, washed with petroleum ether, and dried under vacuum to give benzyl (S)-azetidin-2-one-4-carboxylate (3.85 g) as an off-white solid mp 136°–139° C. The mother liquors and washings are combined, diluted with petroleum ether to 500 ml, seeded, and left in a refrigerator for several days. The resulting precipitate is collected, washed with petroleum ether, and dried under vacuum to give additional product (0.82 g) as pale yellow crystals. Recrystallization of a sample from chloroform-petroleum ether gave the product as small, white flakes: mp 141°–143°; [α]$_D$= −43.4° (c3.275 in CHCl$_3$); IR (CHCl$_3$) 3425, 1778, 1746 cm$^{-1}$; $^1$H NMR (CDCl$_3$) δ3.00 (ddd, 1, J=1.9, 3.2, and 14.6 Hz, H-3a), δ3.35 (ddd, 1, J=1.5, 5.4, and 14.6 Hz, H-3b), δ4.20 (dd, 1, J=3.2 and 5.4 Hz, H-4), δ5.22 (s, 2, OCH$_2$Ph), δ6.48 (m, 1, NH), 7.38 (s, 5, phenyl); mass spectrum m/e 205 (M+), 163, 91, 70, 43.

Anal. Calcd. for C$_{11}$H$_{11}$NO$_3$: C, 64.38; H, 5.40; N, 6.83. Found: C, 64.10; H, 5.70; N, 6.77.

STEP B

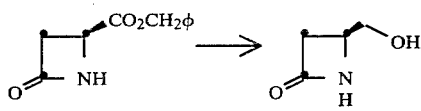

4(S)-4-Hydroxymethylazetidin-2-one

Sodium borohydride (3.69 g, 97.5 mmol) is added in one portion to a suspension of benzyl 4(S)-azetidin-2-one-4-carboxylate (20.0 g, 97.5 mmol) in 300 ml of absolute methanol at 0° C. The mixture is then allowed to warm slowly with periodic cooling being supplied to keep the internal temperature <30° C. After stirring for 2 hr., glacial acetic acid (23.4 g, 390 mmol) is added and the reaction mixture is concentrated under vacuum. The residue is treated with 500 ml of chloroform and filtered. The filtrate is concentrated under vacuum and the residue is chromatographed on 250 g of silica gel (4:1, chloroform:methanol) to yield 9.62 g (98%) of 4(S)-hydroxymethylazetidin-2-one as a white solid: m.p. 51°–53° C.; [α]$_D$= +68.0° (C=2.676 in CHCl$_3$); IR (CHCl$_3$) 3410, 1765 cm$^{-1}$ 1H NMR (CDCl$_3$) δ7.07 (1H, br. s, N<u>H</u>), δ4.05 (1H, br. s, O<u>H</u>), δ3.77 (2H, m H4, H-5a or b), δ3.58 (1H, dd, J=11, 6, H-5a or b), δ2.97 (1H, ddd, J=14.5, 4.8, 1.3, H3b), δ2.7 (1H, br. d, J=14.5, H3a); mass spectrum m/e 101 (M+), 83.

STEP C

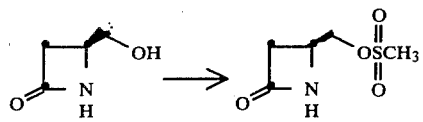

4(S)-4-Methanesulfonyloxymethyl azetidin-2-one

Methane sulfonyl chloride (11.46 g, 100 mmol) is added dropwise by syringe to a solution of 4(S)-4-hydroxymethyl azetidin-2-one (10.1 g, 100 mmol) and triethyl amine (10.1 g, 100 mmol) in 15 ml of dry methylene chloride at 0° C. (Warming is necessary in order to initially solubilize the alcohol. The resulting solution is then cooled to 0° C. prior to addition of the other reagents). The resulting solution is stirred at 0° C. for 1 hr. during which time a voluminous precipitate is produced. At the end of this time, the reaction mixture is filtered and the filtrate is concentrated under vacuum. The two solid residues are combined and treated with 500 ml of chloroform. The resulting mixture is filtered to yield substantially pure 4(S)-4-methanesulfonyloxymethyl azetidin-2-one as a white solid. The filtrate, which contains most of the triethylamine hydrochloride, is concentrated under vacuum and chromatographed on 200 g of silica gel (4:1 chloroform:methanol) to yield an additional quantity of mesylate. This material is combined with that obtained previously and recrystallized from chloroform to yield 15.57 g (87%) of 4(S)-4-methanesulfonyloxymethylazetidin-2-one as colorless needles: m.p. 109.5°–110.5° C.; [α]$_D$= +25.8° (C=1.025 in H$_2$O);

NMR (D$_2$O) δ4.62 (1H, dd, J=11.2, 3.0, H-5a or b), δ4.43 (1H, dd, J=11.2, 6, H-5a or b), δ4.12 (1H, m, H4) δ3.26

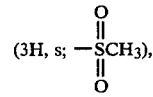

(3H, s; —SCH$_3$),

δ3.19 (1H, dd, J=15, 4.5, H3b).

δ2.88 (1H, dd, J=15, 2.5, H3a); mass spectrum m/e 179 (M+), 136;

Anal: Calc: C, 33.51; H, 5.06; N, 7.82; S, 17.89 Found: C, 33.54; H, 5.08; N, 7.72; S, 17.93

STEP D

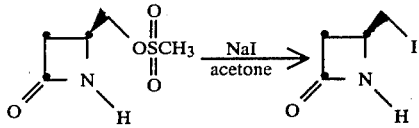

4(S)-4-Iodomethylazetidin-2-one

A mixture of 4(S)-4-methanesulfonyloxy azetidin 2-one (11.8 g, 65.9 mmol) and powdered sodium iodide (19.8 g, 132 mmol) in 130 ml of acetone is heated at reflux for 6 hr. The resulting reaction mixture is concentrated in vacuo, treated with 200 ml of chloroform and filtered. The filtrate is washed with 2×50 ml of water and dried over magnesium sulfate. The organic phase is filtered, concentrated in vacuo, and chromatographed on 250 g of silica gel (ethyl acetate) to yield 11.94 g (86%) of 4(S)-4-iodomethyl-azetidin-2-one as a white solid. This material is recrystallized from ether-petroleum ether to yield white crystals: mp 91°–92° C.; $[\alpha]_D = -23.7°$ (C=1.354 in CHCl$_3$); IR (CHCl$_3$) 3450, 1765 cm$^{-1}$, 1H NMR (CHCl$_3$) δ6.13 (brs, N-H), δ3.94 (m, 1H, Hc), δ3.36 (m, 2H, Hd and e), δ3.16 (ddd, 1H, J=14.9, 5.4, 2.3, Ha), δ2.72 (d, d, d, 1H, J=14.9, 2.1, 2, Hb) mass spectrum m/e 211 (M+), 168, 142, 127, 84.

EXAMPLE 2

Preparation of (4S)-1-(t-Butyldimethylsilyl)-4-iodomethyl-azetidin-2-one

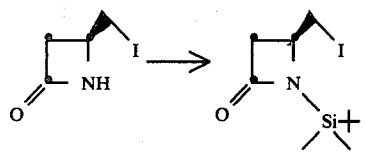

t-butyldimethylchlorosilane (7.51 g, 49.8 mmol) is added in one portion to an ice-cold, stirring solution of (4S)-4-iodomethyl-azetidin-2-one (10.0 g, 47.4 mmol) and triethylamine (5.04 g, 49.8 mmol) in anhydrous dimethylformamide (100 ml). A voluminous white precipitate forms almost immediately. The reaction mixture is stirred at 0°–5° for 1 hour and then allowed to warm to room temperature. Most of the solvent is removed under vacuum to give a residue which is partitioned between diethyl ether (250 ml) and water. The ethereal phase is washed with 2.5 N hydrochloride acid (50 ml), water (3×50 ml), and brine, dried with magnesium sulfate, filtered, and evaporated under vacuum to provide (4S)-1-(t-butyldimethylsilyl)-4-iodomethyl-azetidin-2-one (15.1 g) as a white solid. Recrystallization from petroleum ether-ethyl ether gives the product as colorless plates, mp 71°–72°; n.m.r. (CDCl$_3$), δ3.8 (m, 1), δ2.6–3.6 (2 overlapping d of AB, 4) δ1.0 (S, 9), δ0.3 (S, 6), δ0.25 (S, 6).

EXAMPLE 3

Preparation of Benzyl (4-S)-azetidin-2-one-4-carboxylate

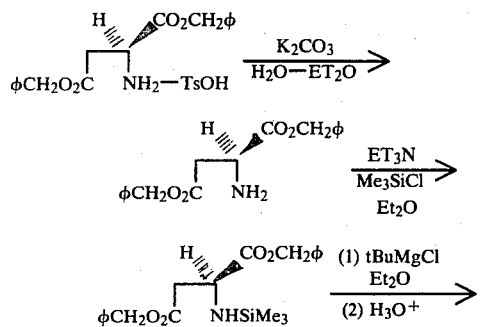

A mixture of dibenzyl (S)-aspartate p-toluenesulfonic acid salt (48.6 g, 0.1 mole), diethylether (300 ml), water (100 ml), and saturated aqueous potassium carbonate (50 ml) is shaken vigorously. The layers are separated and the aqueous portion is extracted with more ether (2×100 ml). The combined ethereal extracts are washed with brine, dried with magnesium sulfate, filtered, and evaporated under vacuum to afford dibenzyl (S)-aspartate (31.5 g) as a water white liquid.

The dibenzyl (S)-aspartate in anhydrous diethyl ether (200 ml) is cooled in an ice bath and stirred under a nitrogen atmosphere while trimethylchlorosilane (12.7 ml, 0.1 mole) and triethylamine (14.0 ml, 0.1 mole) are added successively over a few minutes. The cooling bath is removed and the mixture is stirred at room temperature for 2 hours. The mixture is then filtered under a blanket of nitrogen into a three-neck, one-liter, round bottom flask fitted with a sintered glass funnel, vacuum-nitrogen inlet, and a mechanical stirrer. Additional anhydrous ether (2×50 ml) is used to wash the precipitate of triethylammonium hydrochloride. The funnel containing the precipitate is replaced by a dropping funnel and the etheral filtrate of dibenzyl (4S)-N-trimethyl silyl-aspartate is cooled in an ice bath and stirred under a nitrogen atmosphere while 2.1 M t-butyl magnesium chloride in ether (48 ml, 0.1 mole) is added drop wise over 9 minutes. A gummy precipitate forms during the addition. The cooling bath is then removed and the mixture is allowed to stand at room temperature overnight.

The mixture is cooled in an ice-bath and stirred vigorously while ammonium chloride saturated 2 N hydrochloric acid (100 ml) is added over a few minutes. After stirring vigorously several more minutes, the mixture is diluted with water (100 ml) and ethyl acetate (100 ml) and the layers are separated. The aqueous portion is extracted with ethyl acetate (2×100 ml). The combined organic solution is washed with water (100 ml), 5% aqueous sodium bicarbonate (100 ml), and brine (100 ml), dried with magnesium sulfate, filtered, and evaporated under vacuum to a yellow semi-solid. Crystallization of this material from methylene chloride (100 ml)-petroleum ether (300 ml) provides the azetidinone product (8.2 g) as an off-white powder. The mother liquors are evaporated and the residue crystallized from diethyl ether to afford additional product (2.5 g) as a pale yellow product. The two crops are combined and recrystallized from methylene chloride to yield benzyl (4S)-azetidin-2-one-4-carboxylate (9.5 g) as nearly colorless crystals: mp 139°–141°; $[\alpha]_D = -40.5°$ (C2.0 in CHCl$_3$); IR(CHCl$_3$) 3425, 1778, 1746 cm$^{-1}$; $^1$H NMR (CDCl$_3$) δ3.00 (ddd, H-3β), 3.35(ddd,H-3α), 4.20(dd,H-4), 5.22(s,CH$_2$φ), 6.48(m,NH), 7.35(s,phenyl); mass spectrum m/e 205(M+), 163, 91, 70, 43.

EXAMPLE 4

(4S)-1-(t-butyldimethylsilyl)-4-[2,2-(trimethylenedithia)-2-trimethylsilylethyl]-azetidin-2-one

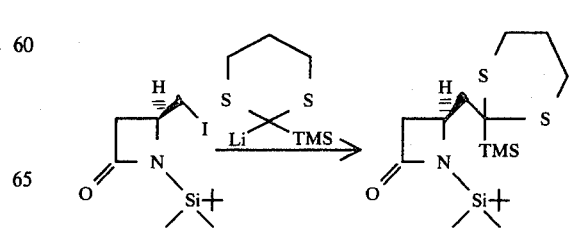

-continued

TMS = trimethylsilyl

A solution of 2-trimethylsilyl-1,3-dithiane (3.78 g, 19.69 mmole) in anhydrous tetrahydrofuran (25 ml) at 0° C. is stirred under nitrogen while n-butyllithium in hexane (20.67 mmol) is added dropwise. The resulting solution is stirred for 15 min. at 0° C. then cooled to −78° C. (dry ice-acetone). A solution of (4S)-1-(t-butyldimethylsilyl)-4-iodomethylazetidin-2-one (6.40 g, 19.69 mmol) in 20 ml of anhydrous tetrahydrofuran is added slowly by syringe over ca. 5 min. The resulting solution is stirred at −78° C. for 1 hr., then quenched by the addition of saturated aqueous ammonium chloride solution (10 ml) and allowed to warm to room temperature (22° C.). The mixture is poured into a separatory funnel containing ethylether (200 ml) and water (100 ml). The organic phase is separated, washed with brine and dried over anhydrous magnesium sulfate. The solvent is removed in vacuo to yield a yellow oil. This material is filtered through a short silica gel column (25% ether in petroleum ether) to give 6.15 g (80%) of (4S)-1-(t-butyl-dimethylsilyl)-4-[2,2-(trimethylenedithia)-2-trime-thysilylethyl]-azetidin-2-one as a white solid, m.p. 71°–73° C. n.m.r. (CDCl₃) δ3.9 (1H, m, H-5), 2.2–3.6 (8H, overlapping m), δ2.0(2H, m, SCH₂CH₂CH₂S), δ0.99 (9H, S, ±Si), δ0.23(15H, br.S, (CH₃)₂Si & (CH₃)₃Si).

IR (CHCl₃) 2930, 2855, 1723 cm⁻¹.

EXAMPLE 5

(3,R,S,4R)-1-(t-Butyldimethylsilyl)-3-[(R,S)-1-hydrox-yethyl]-4-[2,2-(trimethylenedithia)-2-trimethylsilyle-thyl]-azetidin-2-one

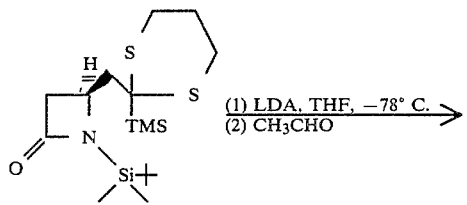

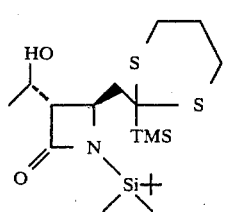

A solution of diisopropylamine (10.5 mmol) in anhydrous tetrahydrofuran (40 ml) is cooled to −78° C. (dry ice-acetone) and stirred under nitrogen atmosphere while n-butyllithium in hexane (10.5 mmol) is added slowly by syringe. After 15 min., a solution of (4S)-1-(t-butyldimethylsilyl)-4-[2,2-(trimethylenedithia)-2-trime-thylsilyl ethyl]-azetidin 2-one (10.0 mmol) in anhydrous tetrahydrofuran (12 ml) is added slowly by syringe. The resulting solution is stirred at −78° C. for 20 min. prior to the addition of acetaldehyde (30.0 mmol). After an additional 10 min. at −78° C. the reaction is quenched by the addition of saturated aqueous ammonium chloride solution (10 ml) and allowed to warm to room temperature. The reaction mixture is diluted with ethyl acetate (150 ml) and washed with 2.5 N hydrochloric acid solution (50 ml), water (50 ml) and brine (50 ml) and dried over magnesium sulfate. Removal of solvents in vacuo gives a white solid (4.6 g) which is chromatographed on 250 g of silica gel (1:1, ether; petroleum ether) to give four main product fractions with a total weight of 4.185 g (96.7%). Fraction No. 1-R_f=0.62, 85 mg. Fraction No. 2-R_f=0.43, 1.95 g (45%), (3S,4R)-1-(t-butyldimethyl-silyl)-3-[(S)-1-hydroxyethyl]-4-[2,2-(trimethylenedithia]-2-trimethylsilylethyl]-azetidin-2-one. Fraction No. 3-R_f=0.34, 150 mg. mixture. Fraction No. 4-R_f=0.28, 2.0 g (46%), (3S,4R)-1-(tributyl-dimethylsilyl)-3-[(R)-1-hydroxyethyl]-4-[2,2-(trime-thylenedithia)-2-trimethylsilylethyl]-azetidin-2-one.

EXAMPLE 6

(3S,4R)-1-(t-Butyldimethylsilyl)-3-(1-oxoethyl)-4-[2,2-(trimethylenedithia)-2-trimethylsilylethyl]azetidin-2-one Step A:

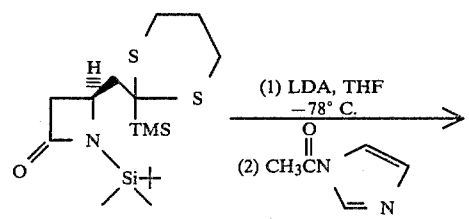

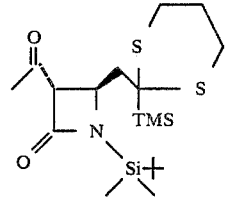

A solution of diisopropylamine (6.0 mmol) in anhydrous tetrahydrofuran (25 ml) is cooled to −78° C. (dry ice-acetone) and stirred under a nitrogen atmosphere while n-butyllithium in hexane (6.0 mmol) is added by syringe. After 15 min., a solution of (4S)-1-(t-butyldimethyl-silyl)-4-[2,2-(trimethylenedithia)-2-trimethylsilylethyl]-azetidin-2-one (3.0 mmol) in anhydrous tetrahydrofuran (3 ml) is added dropwise by syringe. The resulting solution is stirred at −78° C. for 30 min., then added through a Teflon tube to a mixture of N-acetylimidazole (6.0 mmol) and anhydrous tetrahydrofuran (25 ml) at −78° C. The resulting yellow reaction mixture is stirred at −78° C. for 10 min., then quenched by addition of saturated aqueous ammonium chloride solution. The reaction mixture is poured into ether (200 ml) and extracted with 2.5 N hydrochloric acid solution (50 ml), water (50 ml) and brine and dried over magnesium sulfate. Removal of solvents in vacuo gives a yellow oil which is chromatographed on silica gel (ether-petroleum ether) (1:2) to yield (3S,4R)-1-(t-butyldime-thylsilyl)-3-(1-oxoethyl)-4-[2,2-(trimethylenedithia) 2-trimethysilylethyl]-azetidin-2-one.

Step B:

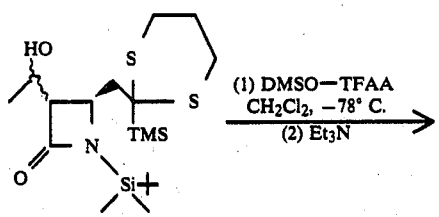

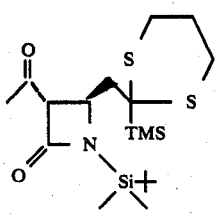

Trifluoroacetic anhydride (6.0 mmol) is added by syringe to a solution of dimethylsulfoxide (8.0 mmol) in anhydrous methylene chloride (10 ml) at −78° C. The resulting mixture is stirred at −78° C. for 20 min., during which time a white precipitate forms. A solution of (3RS, 4R)-1-(t-butyldimethylsilyl)-3-(RS-1-hydroxyethyl)-4-[2,2-(trimethylenedithia)-2-trimethylsilylethyl]-azetidin-2-one (4.0 mmol) in anhydrous methylene chloride (10 ml) is added by syringe and the resulting mixture is stirred at −78° C. for 40 min. Triethylamine (11.2 mmole) is added by syringe and the cooling bath is removed. After 1 hr. the reaction mixture is diluted with CH$_2$Cl$_2$ (100 ml) and washed with 2.5 N hydrochloric acid solution (50 ml), water (50 ml) and brine and dried over magnesium sulfate. Purification as above yields (3S, 4R)-1-(t-butyldimethylsilyl)-3-(1-oxoethyl)-4-[2,2-trimethylenedithia)-2-trimethylsilylethyl]-azetidin-2-one. n.m.r. (CDCl$_3$) 4.23 (1H, BrS, H-6), δ4.2 (1H, m, H-5), δ2.1–3.2 (6H, m), δ2.27 (3H, s, CH$_3$-C=O), δ2.0 (2H, m, SCH$_2$CH$_2$CH$_2$S), δ0.96 (9H, S, ±Si), δ0.25 (15H, br.S (CH$_3$)$_2$Si & (CH$_3$)$_3$Si).

EXAMPLE 7

(3S, 4R)-1-(t-Butyldimethylsilyl)-3-[(R)-1-hydroxyethyl]-4-[2,2-(trimethylenedithia-2-trimethylsilylethyl]azetidin-2-one

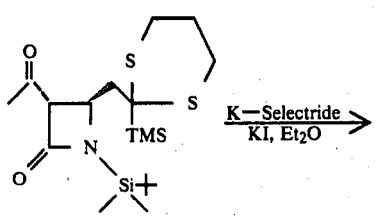

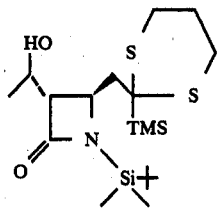

K-Selectride (potassium tri-sec-butylborohydride) (4.8 mmol) in a solution of tetrahydrofuran is added dropwise by syring to a mixture of (3S, 4R)-1-(t-butyldimethylsilyl)-3-(1-oxoethyl)-4-[2,2-(trimethylenedithia)-2-trimethylsilylethyl]-azetidin-2-one (2.0 mmol) and potassium iodide (2.0 mmol) in anhydrous ether (20 ml) at room temperature. The resulting mixture is stirred at room temperature for 2.5 hr., then quenched by addition of glacial acetic acid (9.6 mmol). The resulting mixture is diluted with ethyl acetate (50 ml) and filtered through celite. The solvents are removed in vacuo to give an oil which is chromatographed on silica gel (1:1, ether: petroleum ether) to give (3S, 4R)-1-(t-butyldimethylsilyl)-3-[(R)-1-hydroxyethyl]-4-[2,2-(trimethylenedithia)-2-trimethylsilylethyl]-azetidin-2one as a white solid, n.m.r. (CDCl$_3$+D$_2$O) δ4.23 (1H, dq, J=7.5,7,H-8) δ3.78(1H, ddd, J=7.5, 3, 2.2, H-5) δ3.18 (1H, dd, 7.5, 2.2, H-6), δ2.5–3.0 (4H, m, -SCH$_2$CH$_2$CH$_2$S- δ2.35

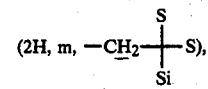

(2H, m, —CH$_2$—S),

δ2.0 (2H, m, SCH$_2$CH$_2$CH$_2$S) δ1.33 (3H, d, J=7, CH$_3$-), δ0.98 (9H, S, ±Si) δ0.26 (15H, br.S, (CH$_3$)$_2$Si+ (CH$_3$)$_3$Si).

EXAMPLE 8

(3S, 4R)-1-(t-Butyldimethylsilyl)-3-[(R)-1-hydroxyethyl]-4-(2-oxo-2-trimethylsilylethyl)-azetidin-2-one

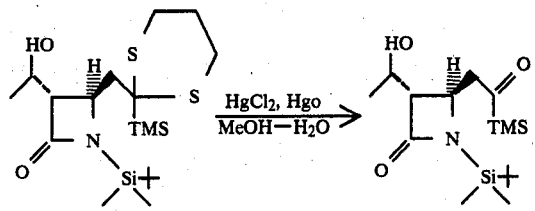

A mixture of mercuric oxide (6.93 mmol), mercuric chloride (10.2 mmol) and (3S, 4R)-1-(t-butyldimethylsilyl)-3-[(R)-1-hydroxyethyl]-4-[2,2-(trimethylenedithia)-2-trimethylsilylethyl]-azetidin-2-one (4.62 mmol) in 5% aqueous methanol (25 ml) is heated at reflux for 45 min. During this time, the color of reaction mixture changes from orange to off-white. The mixture is cooled and filtered and the filter cake is washed several times with methanol. The combined filtrate and washings are concentrated to ~5 ml in vacuo, then diluted with ethyl acetate (100 ml) and washed with saturated aqueous ammonium chloride solution (2×50 ml) and brine. The organic phase is dried over magnesium sulfate and concentrated in vacuo to yield a pale yellow oil. This material is chromatographed on silica gel (ether) to yield (3S, 4R)-1-(t-butyldimethylsilyl)-3-[(R)-1-hydroxyethyl]-4(2-oxo-2-trimethylsilylethyl)-azetidin-2-one, 1.38 g (87%), as a white solid, m.p. 82°–84° C. n.m.r. (CDCl₃-D₂O) δ3.6–4.3 (2H, m, H-5, H-8) δ3.12(2H, center of d of AB, J=18, 4, 8.5,

δ2.7 (1H, dd, J=7.5,2, H-6), δ1.27 (3H, d, J=6.5, CH₃-) δ0.99 (9H, s, ±Si), δ0.3(15H, br.S, (CH₃)₃ Si & (CH₃)₂Si). I.R. (CHCl₃) 3450, 2930, 2855, 1737, 1635 cm⁻¹.

EXAMPLE 9

(3S,4R)-1-(t-Butyldimethylsilyl)-3-[(R)-1-hydroxyethyl]-4-carboxymethyl-azetidin-2-one

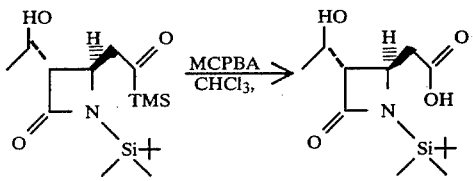

m-Chloroperbenzoic acid (1.00 mmol) is added to a solution of (3S,4R)-1-(t-butyldimethylsilyl-3-[(R)-1-hydroxyethyl]-4-(2-oxo-2-trimethylsilylethyl)-azetidin-2-one (1.00 mmol) in chloroform (4 ml). The resulting solution is heated at reflux for 4 hr, then cooled, concentrated in vacuo, and the residue chromatographed on silica gel (2% glacial acetic acid in methylene chloride). (3S, 4R)-1-(t-butyldimethylsilyl)-3-[(R)-1-hydroxyethyl]-4-carboxymethyl-azetidin-2-one, 238 mg (83%) is isolated as a colorless solid, R_f=0.25. n.m.r. (CDCl₃ & D₂O) δ3.6–4.3 (2H, m, H-5, H-8), δ2.98 (1H, dd, J=7, 2.1 H-6), δ2.7(2H, d of ABq)-CH₂CO₂H), δ1.29 (3H, d, J=6, CH₃—) δ0.95 (9H, S, Si±), δ0.25 (6H, S, (CH₃)₂-Si).

EXAMPLE 10

(3S, 4R)-1-(t-Butyldimethylsilyl)-3-[(R)-1-hydroxyethyl]-4-(3-p-nitrobenzyloxycarbonyl-2-oxopropyl)-azetidin-2-one

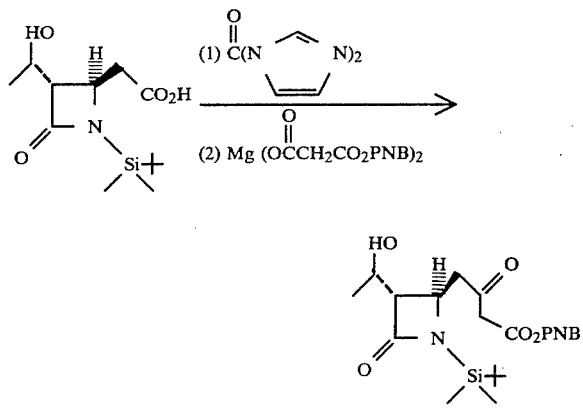

1,1'-Carbonyldimidazole (1.10 mmol) is added in one portion to a solution of (3S, 4R)-1-(t-butyldimethylsilyl-3-[(R)-1-hydroxyethyl]-4-carboxymethyl-azetidin-2-one (1.0 mmol) in anhydrous tetrahydrofuran (5 ml) at room temperature. The resulting solution is stirred at room temperature for 6 hours. In a second flask, magnesium ethoxide (5 mmol) is added in one portion to a solution of the mono-p-nitrobenzyl ester of malonic acid (10 mmol) in anhydrous tetrahydrofuran (25 ml). The resulting mixture is stirred at room temperature for 1 hr, then the tetrahydrofuran is removed at the pump and the gummy residue is triturated with ether to yield the magnesium salt as an off-white solid. (1.1 mmol) of this magnesium salt is then added to the first reaction flask and the resulting mixture is stirred at room temperature for 18 hrs. The reaction mixture is then poured into 50 ml of ether, washed with 0.5 N hydrochloric acid solution (20 ml), water (20 ml), saturated aqueous sodium bicarbonate solution (20 ml), brine and dried over magnesium sulfate. Removal of solvents in vacuo gives an oil which is chromatographed on silica gel (ether) to yield (3S,4R)-1-(t-butyldimethylsilyl)-3-[(R)-1-hydroxyethyl]-4-(3-p-nitrobenzyloxycarbonyl-2-oxopropyl)-azetidin-2-one. n.m.r. (CDCl₃-H₂O) δ8.24, 8.10, 7.52, 7.38(2H, AB, aromatic), δ5.26 (2H, S, -CH₂-AR), δ3.5–4.2 (2H, m, H-5, H-8), δ2.6–3.3 (3H, m, H-6,

δ1.3 (3H, d, J=6.6, CH₃-) δ0.98 (9H, S, ±Si-) δ0.25 (6H, S, (CH₃)₂Si<).

EXAMPLE 11

(3S,4R)-3-[(R)-1-hydroxyethyl]-4-(3-p-nitrobenzyloxycarbonyl-2-oxopropyl)-azetidin-2-one

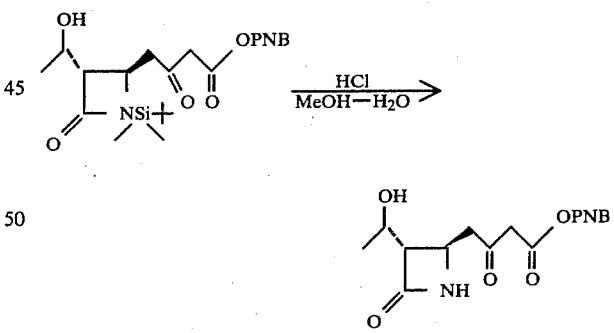

A solution of (3S, 4R)-1-(t-butyldimethylsilyl)-3-[(R)-1-hydroxyethyl]-4-(3-p-nitrobenzyloxycarbonyl-2-oxopropyl)-azetidin-2-one (1.0 mmol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs, at room temperature the reaction mixture is diluted with ethyl acetate (25 ml), washed with water (10 ml) and brine, dried over magnesium sulfate and concentrated in vacuo to yield (3S, 4R)-3-[(R)-1-hydroxyethyl]-4-(3-p-nitrobenzyloxycarbonyl-2-oxopropyl)-azetidin-2-one.

EXAMPLE 12

Preparation of (3S, 4R)-3-[(R)-1-hydroxyethyl])-4-[3-(4-nitrobenzyl)oxycarbonyl-2-oxo-3-diazopropyl]azetidin-2-one

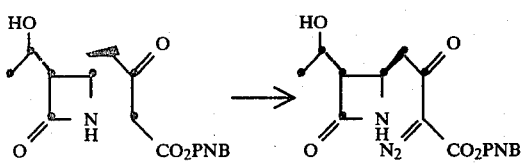

Triethylamine (263 mg, 2.6 mmol) is added by syringe to a mixture of (3S, 4R)-3-[(R)-1-hydroxyethyl]-4-[3-(4-nitrobenzyl)oxycarbonyl-2-oxopropyl]azetidin-2-one (253 mg, 0.72 mmol) and p-carboxybenzene sulfonylazide (196 mg, 0.84 mmol) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 222 mg., (81% overall from (3S, 4R)-1-(t-butyldimethylsilyl)-3-[(R)-1-(t-butyl dimethylsilyloxy)ethyl]-4-[3-(4-nitrobenzyl)oxycarbonyl-2-oxopropyl]azetidin-2-one) of (3S, 4R)-3-(R)-1-hydroxyethyl]-4-[3-(4-nitrobenzyl)-oxycarbonyl-2-oxo-3-diazopropyl]azetidin-2-one as a white solid m.p. (dec.) 163° C. IR(CHCl₃, CM⁻¹) 3410, 2132, 1756, 1718, 1650, 1350, 1280, 1120; n.m.r. (CDCl₃) δ7.9 (2d-aromatic, 4), δ5.4(s,2), δ6.2(brs, 1), δ4.1(m, 2), δ2.6-3.6(m, 4), δ1.32(d, 3, J=6.2).

EXAMPLE 13

Preparation of (5R,6S)p-Nitrobenzyl 6-[(R)-1-hydroxyethyl]-1-azabicyclo[3.2.0]heptan-3,7-dione-2-carboxylate

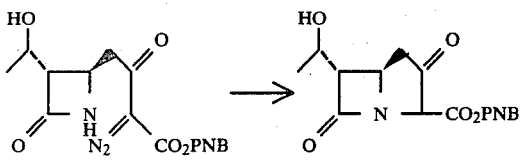

A suspension of (3S,4R)-3-[(R)-1-hydroxyethyl]-4-[3-(4-nitrobenzyl)oxycarbonyl-2-oxo-3-diazopropyl]azetidin-2-one (56.4 mg, 0.15 mmol) and rhodium (II) acetate (0.1 mg) in dry benzene (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield (5R, 6S) p-nitrobenzyl 6-[(R)-1-hydroxyethyl]-1-azabicyclo[3.2.0]heptan-3,7-dione-2-carboxylate 51 mg (98%) as a colorless oil which slowly crystallized at room temperature (22° C.).

Physical Properties:

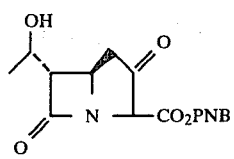

-continued
Physical Properties:

PNB = p-nitrobenzyl n.m.r.: (300 MHz, CDCl₃) δ8.26, 7.54(aromatic, 4), 5.29 (AB,2), 4.77 (s,1), 4.32(dg,I,J=6.6,7), 4.16(ddd,1,J=7,7.5,2.2), 3.21(dd,1,J=7,2.2), 2.94(dd,1,J=19.5,7) 2.50(dd,1,J=19.5,7.5), 2.2(brs,1), 1.37(d,3,J=6.6).
I.R.: (CHCl₃,CM⁻¹) 1770, 1758, 1610, 1522, 1353
m.p. 110°–111° C.

EXAMPLE 14

Preparation of p-Nitrobenzyloxycarbonylaminoethanethiol

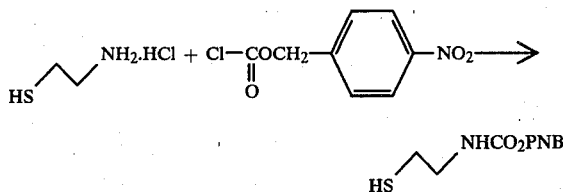

To 600 ml diethyl ether (Et₂O)—75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl₃): 8.18 (d, J=8 Hz, aromatic protons ortho to nitro), 7.47 (d, J=8 Hz, aromatic protons meta to nitro), 5.27 (—NH—), 5.20 (s, CH₂—NH—), 2.67 (m, —CH₂—SH), 1.35 (t, J=8.5 Hz, —SH) in ppm downfield from TMS. IR (CHCl₃ solution): carbonyl- 1725 cm⁻¹. M.S.: molecular ion-256, (M-47) at 209, (M-136) at 120, ⁺CH₂φpNO₂ at 136.

EXAMPLE 15

Preparation of (5R,6S) p-Nitrobenzyl 3-[2-(p-nitrobenzyloxycarbonyl)aminoethylthio]-6-[(R)-1-hydroxyethyl]-1-azabicyclo[3.2.0]hept-2-en-7-one-2-carboxylate

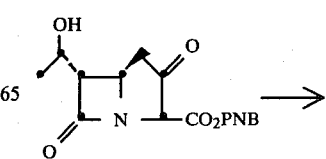

-continued

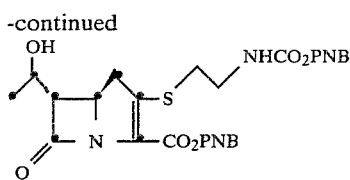

(5R,5S) p-Nitrobenzyl 6-[(R)-1-hydroxyethyl]-1-azabicyclo[3.2.0]heptan-3,7-dione-2-carboxylate (51 mg, 0.147 mmol) is dissolved in acetonitrile (3 ml) and the resulting solution is cooled to 0° C. Diisopropylethylamine (22 mg, 0.17 mmol) is added by syringe and the resulting solution is stirred at 0° C. for 1 minute prior to the addition of a solution of freshly recrystallized p-toluene sulfonic anhydride (51 mg, 0.156 mmol) in dry acetonitrile (1 ml). The resulting solution is stirred at 0° C. for 1 hour to provide (5R, 6S)p-nitrobenzyl 3-(p-toluenesulfonyloxy)-6-[(R)-1-hydroxyethyl]-1-azabicyclo[3.2.0]hept-2-en-7-one-2-carboxylate, then cooled to −25° C. Diisopropylethylamine (80.5 mg, 0.624 mmol) is added by syringe followed shortly thereafter by a solution of N-p-nitrobenzyloxycarbonylcysteamine (40 mg, 0.156 mmol) in 1 ml of dry acetonitrile. The reaction mixture is then stored in a refrigerator for 70 hr. The mixture is diluted with 25 ml of ethyl acetate washed with brine and dried over magnesium sulfate. Solvents are removed in vacuo to yield a yellow oil which is chromatographed on a silica gel plate (ethyl acetate, $R_f$=0.4) to yield (5R,6S) p-nitrobenzyl-3-[2-(p-nitrobenzyloxycarbonyl)aminoethylthio]-6-[(R)-1-hydroxyethyl]-1-azabicyclo [3.2.0]-hept-2-en-7-dione-2-carboxylate as a yellow solid, m.p. 167°–169° C. IR(-Nujol mull) 1773 and 1690 cm$^{-1}$; n.m.r. (CDCl$_3$) $\delta$7.54–8.26 (overlapping ABq,4), $\delta$5.40(ABq,2), $\delta$5.22(s,2), $\delta$4.27(m,2), $\delta$3.47(m), $\delta$3.23(dd, 1), $\delta$3.14(dd, 1) $\delta$3.40(dd,1), $\delta$3.04(m,2), $\delta$1.37(d, 3).

EXAMPLE 16

Preparation of Thienamycin

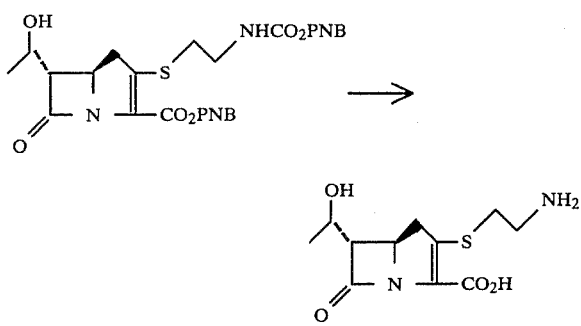

A mixture of N-p-nitrobenzyloxycarbonyl thienamycin p-nitrobenzyl ester (10 mg, 0.017 mmol) and 10% Pd/C-Bolhofer type in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water (3×3 ml). The combined filtrate and washings are extracted with ethyl acetate-ethyl ether then concentrated to ~3 ml and lyophilized. The resulting white powder is identical to natural thienamycin in all respects.

EXAMPLE 17

Preparation of

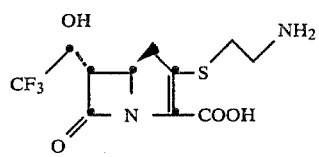

5R, 6S, 8S

Step A:

(3S, 4R)-1-(t-Butyldimethylsilyl)-3-(1-oxo-2,2,2-trifluoroethyl)-4-[2,2-(trimethylenedithia)-2-trimethylsilylethyl]-azetidin-2-one

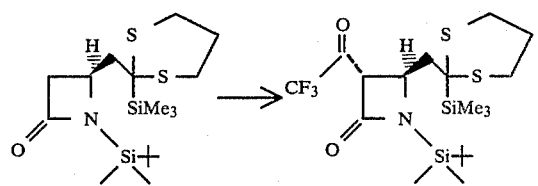

A solution of diisopropylamine (41.1 mmol) in freshly distilled tetrahydrofuran (200 ml) is cooled to −78° C. and stirred under a nitrogen atmosphere while n-butyllithium in hexane (41.1 mmole) is added by syringe. After 15 minutes, a solution of (4S)-1-(t-butyldimethylsilyl)-4-[2,2-(trimethylenedithia)-2-trimethylsilylethyl]azetidin-2-one (18.69 mmol) in dry tetrahydrofuran (20 ml) is added slowly by syringe. The resulting solution is stirred at −78° C. for 30 minutes, then added through a Teflon tube to a solution of S-ethyltrifluoromethylthioacetate (41.1 mmol) in tetrahydrofuran (120 ml). The total time required for the addition is 8 minutes. The resulting solution is stirred at −78° C. for an additional 10 minutes, then quenched by the addition of saturated aqueous ammonium chloride solution (50 ml). The reaction mixture is then diluted with ether (500 ml) and washed with 50 ml of 2.5 N hydrochloric acid solution. The phases are separated and the aqueous phase is backwashed with ether (100 ml). The organics are combined, washed with water (100 ml) and brine (100 ml) and dried over anhydrous magnesium sulfate. The resulting solution is decolorized by brief heating with activated charcoal and the solvents are removed in vacuo to give an off-white solid (9.6 mg). This material is recrystallized from petroleum ether to give 7.03 g (78%) of white crystals, m.p. 120.5°–122.5° C.

I.R. (CHCl$_3$, cm$^{-1}$) 1767, 1736, 1318 N.M.R. (CDCl$_3$) $\delta$4.6(1H, d, J=2.6 Hz, H$_3$), 4.2 (1H, ddd, J=2.6, 6.5, 8.8 Hz, H$_4$), 2.3-3.2 (6H, m), 2.0 (2H, m, —SCH$_2$CH$_2$CH$_2$S—), 0.9 (9H, S, tBuMe$_2$Si—), 0.2 (6H, 2S, tBuMe$_2$Si) 0.16 (9H, S, Me$_3$Si) Mass spectrum (m/e) 485, 412, 388

Step B:

(3S, 4R)-1-(t-Butyldimethylsilyl)-3-[(S)-1-hydroxy-2,2,2-trifluoroethyl]-4-[2,2-(trimethylenedithia)-2-trimethylsilylethyl]azetidin-2-one

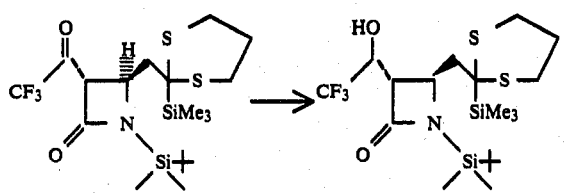

A partial suspension of sodium borohydride (10.0 mmol) in isopropanol (10 ml) is added rapidly to a solution of (3S, 4R)-1-(t-butyldimethylsilyl)-3-(1-oxo-2,2,2-trifluoroethyl)-4-[2,2-(trimethylenedithia)-2-trimethylsilylethyl]-azetidin-2-one (10.0 mmol) in anhydrous tetrahydrofuran (50 ml) at −78° C. The resulting mixture is stirred at −78° C. for 30 min. then allowed to warm to room temperature. Excess sodium borohydride is decomposed by recooling the reaction mixture to 0° C. and carefully adding 2.5 N hydrochloric acid solution (20 ml). The reaction mixture is then poured into ether (250 ml), washed with water (50 ml) and brine (50 ml) and dried over anhydrous magnesium sulfate. Removal of solvents in vacuo gives a colorless oil which is chromatographed on silica gel (150 g), (2:1 petroleum ether:ether) to provide 3.24 g (66.8%) of (3S, 4R)-1-(t-butyldimethylsilyl)-3-[(S)-1-hydroxy-2,2,2-trifluoroethyl]-4-[2,2-trimethylenedithia)-2-trimethylsilylethyl]-azetidin-2-one. IR (CHCl$_3$, cm$^{-1}$) 3320, 1745, 1332. NMR (CDCl$_3$) δ4.45 (1H, brS, O$\underline{H}$), 3.9–4.9 (2H, overlapping m, H$_5$+H$_8$), 3.4 (1H, dd, J=9, 2.3, H6), 2.8 (4H, m), 2.4 (2H, m), 2.0 (2H, m), 1.0(9H, S, tBuMe$_2$Si), 0.3 (15H). This reaction also provides 1.04 g (21.3%) of the 8-R epimer of the above compound.

Step C:

(3S, 4R)-1-(t-Butyldimethylsilyl)-3-[(S)-1-hydroxy-2,2,2-trifluoroethyl]-4-(2-oxo-2-trimethylsilylethyl)-azetidin-2-one

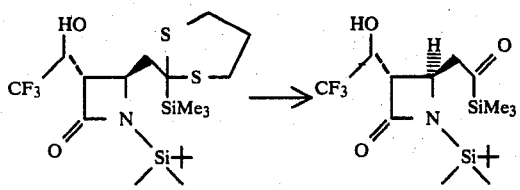

Mercuric oxide (10.8 mmol) and mercuric chloride (15.8 mmol) are added successively to a solution of (3S, 4R)-1-(t-butyldimethylsilyl)-3-[(S)-1-hydroxy-2,2,2-trifluoroethyl]-4-[2,2-(trimethylenedithia)-2-trimethylsilylethyl]-azetidin-2-one (7.19 mmol) in 5% aqueous methanol (70 ml). The resulting mixture is heated at reflux for 1 hr, then cooled to room temperature and filtered. The filter cake is washed with additional methanol (2×30 ml) and the combined filtrate and washings are concentrated in vacuo. The residue is dissolved in ether (150 ml) and washed with saturated aqueous ammonium chloride solution (2×50 ml) The aqueous phase is backwashed with ether (100 ml) and the combined organics are washed with brine (50 ml) and dried over anhydrous magnesium sulfate. Removal of solvents in vacuo gives 2.94 g of an off-white solid. This material is chromatographed on silica gel (120 g, eluted with 3:2 petroleum ether:ether) to give 2.47 g (87%) of a white solid, m.p. 83°–85° C. IR (CHCl$_3$, cm$^{-1}$) 3360, 1740, 1635, 1333. NMR (CDCl$_3$+D$_2$O) δ3.9–4.5 (2H, overlapping m, H5 and H8), 3.0 (2H, 2dd, J=18, 4.4, J=18, 7.2, H1 a+b), 3.2 (1H, dd, J=2.7, 5.5, H6), 1.0 (9H, S, t-BuMe$_2$Si—), 0.2(15H, t-BuMe$_2$Si— and Me$_3$Si).

Step D:

(3S, 4R)-1-(t-Butyldimethylsilyl)-3-[(S)-1-hydroxy-2,2,2-trifluoroethyl]-4-carboxymethyl-azetidin-2-one

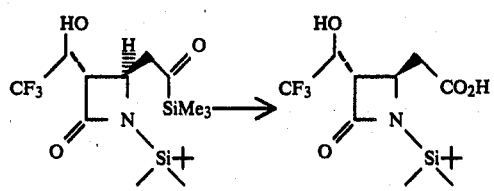

A solution of (3S, 4R)-1-(t-butyldimethylsilyl)-3-[(S)-1-hydroxy-2,2,2-trifluoroethyl]-4-(2-oxo-2-trimethylsilylethyl)-azetidin-2-one (2.52 mmol) and 30% hydrogen peroxide (12.6 mmol) in methanol (2.5 ml) is heated at 45°–50° C. for 3 hr. The reaction mixture is then cooled to 0° C. and dimethylsulfide (1 ml) is added. The ice bath is removed and the reaction mixture is monitored with starch iodide paper. When no oxidizing agent remains, the reaction mixture is concentrated in vacuo and the residue is dissolved in 2:1 petroleum ether:ether (100 ml) and washed with water (3×15 ml), then dried over anhydrous magnesium sulfate. Removal of solvents in vacuo gives 861 mg of a white solid which is recrystallized from petroleum ether-ether to yield 745 mg (87%) of white crystals, m.p. 134°–136° C.

IR (CHCl$_3$, cm$^{-1}$) 3350 (very broad), 1738(br), 1335. NMR (acetone-d6) δ4.2–4.7 (2H, overlapping multiplets, H5 and H8), 3.65 (1H, dd, H6), 2.8 (2H, br.d, H1 A+B), 1.0 (9H, S, t-BuMe$_2$Si—) 0.3 (6H, 2d, tBuMe$_2$Si—).

Step E:

Following the procedure of Examples 10–16 except substituting an equivalent amount of the azetidinone of Example 17, Step D, for the azetidinone of Example 10, there is obtained:

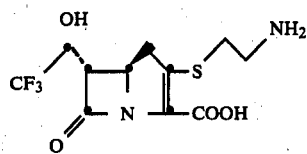

5R, 6S, 8S

EXAMPLE 18

Following the procedures of the foregoing Examples and text, the azetidinones of Table I are obtained; appropriate annotation is provided under the 'Remarks' column.

TABLE I

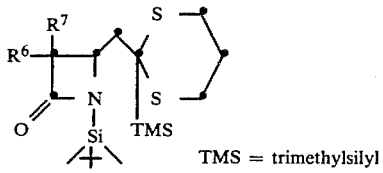

TMS = trimethylsilyl

| Compound | R⁶ | R⁷ | Remarks |
|---|---|---|---|
| (1.) | $(CH_3)_2CH$ | H | As in Example 5, but substitute equivalent amount of isopropyl iodide for acetaldehyde. |
| (2.) | $CH_3$ | H | As in Example 5, but using an equivalent amount of methyl iodide for acetaldehyde. |
| (3.) | $HOCH_2$ | $CH_3$ | As in Example 5, but use compound 2., and excess formaldehyde introduced as a gas just above surface of stirred solution. |
| (4.) | $\phi CH_2\overset{\underset{\mid}{OH}}{C}H$  $\phi = $ phenyl | H | As in Example 5, but using an equivalent amount of phenyl acetaldehyde for acetaldehyde. |
| (5.) | $CH_3\overset{\underset{\mid}{OH}}{C}H$ | $CH_3$ | Using the procedure of Example 5 upon compound 2 of Table I. |
| (6.) | $\phi CH_2$ | H | As in Example 5, but substitute benzylbromide for acetaldehyde. |
| (7.) | $CH_3\overset{\underset{\mid}{OH}}{C}H$ | $\phi CH_2$ | As in Example 5, but using compound 6 as substrate. |
| (8.) | $CH_3\overset{\underset{\mid}{OMs}}{C}H$  Ms = mesyl | H | Obtained from the product of Example 5 and methanesulfonyl chloride and triethylamine in methylene chloride at 0°. |
| (9.) | $CH_3\overset{\underset{\mid}{N_3}}{C}H$ | H | Obtained from compound 8 on treatment with $LiN_3$ in DMF at 60°. |
| (10.) | $CH_3\overset{\underset{\mid}{NH_2}}{C}H$ | H | Obtained from compound 9 by reduction with $H_2S$ and $Et_3N$ in $CH_2Cl_2$. |
| (10a.) | $CH_3\overset{\underset{\mid}{NHCO_2PNB}}{C}H$ | H | Obtained from compound 9 on treatment with $ClCO_2PNB$ and DMPA in $CH_2Cl_2$ at 0°. |
| (11.) | $(CH_3)_2CH\overset{\underset{\mid}{OH}}{C}H$ | H | As in Example 5, but substituting isobutyraldehyde for acetaldehyde. |

TABLE I-continued

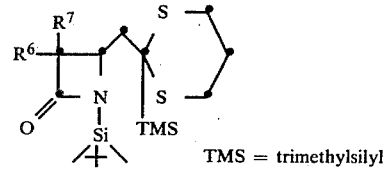

TMS = trimethylsilyl

| Compound | R⁶ | R⁷ | Remarks |
|---|---|---|---|
| (12.) | $(CH_3)_2CHCH_2CH_2\overset{\underset{\mid}{OH}}{C}H$ | H | As in Example 5, but substitute 5-methyl valeraldehyde for acetaldehyde |
| (13.) | $\triangleright\!\!-\overset{\underset{\mid}{OH}}{C}H$ | H | As in Example 5, but substitute cyclopropane carboxaldehyde for acetaldehyde. |
| (14.) | $CF_3\overset{\underset{\mid}{OH}}{C}H$ | $CH_3$ | As in Example 5, but substitute trifluoroacetaldehyde for acetaldehyde. |
| (15.) | $tBuMe_2SiOCH_2\overset{\underset{\mid}{OH}}{C}H$ | H | As in Example 5, but substitute t-butyldimethylsilyloxyacetaldehyde for acetaldehyde. |
| (16.) | $HOCH_2CH_2$ | H | As in Example 5, but substitute oxirane for acetaldehyde. |
| (17.) | $CH_3CH_2CH_2\overset{\underset{\mid}{OH}}{C}H$ | H | As in Example 5, but substitute butyraldehyde for acetaldehyde. |
| (18.) | $CH_3CH_2\overset{\underset{\mid}{OH}}{C}H$ | H | As in Example 5, but substitute propionaldehyde for acetaldehyde. |
| (19.) | $FCH_2\overset{\underset{\mid}{OH}}{C}H$ | H | As in Example 5, but substitute fluoroacetaldehyde for acetaldehyde. |
| (20.) | $\triangleright\!\!-CH_2\overset{\underset{\mid}{OH}}{C}H$ | H | As in Example 5, but substitute cyclopropylacetaldehyde for acetaldehyde. |
| (21.) | $CH_3CH_2$ | H | As in Example 5, but substitute ethyliodide for acetaldehyde. |
| (22.) | $CH_3$ | $CH_3$ | As in Example 5, but use compound 2 and substitute methyliodide for acetaldehyde. |
| (23.) | $\triangleright\!\!-CH_2$ | H | As in Example 5, but substitute cyclopropylmethylbromide for acetaldehyde. |
| (24.) | $HOCH_2CH_2$ | $CH_3$ | As in Example 5, but use compound 2 and substitute oxirane for acetaldehyde. |
| (25.) | $\overset{\underset{\mid}{OH}}{\pentagon}$ | H | As in Example 5, but use cyclopentanone instead of acetaldehyde. |

TABLE I-continued

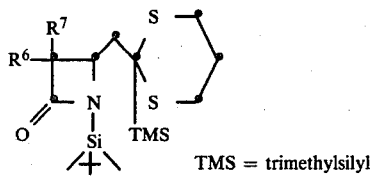

TMS = trimethylsilyl

| Compound | R$^6$ | R$^7$ | Remarks |
|---|---|---|---|
| (25a) | ClCH$_2$—CH(OH)— | H | As in Example 17, Steps A & B, (or, equivalently, the procedure of Exs. 6 & 7) but use an equivalent amount of chloroacetyl-imidazole instead of S—ethyltrifluoro-methylthioacetate. |
| (25b) | ClCH$_2$—CH(OH)— | CH$_3$ | As in Example 18, Table I, No. 25a, but starting with azetidinone of Example 18, Table I, No. 3. |
| (26.) | H$_2$CFC(=O)— | H | As in Example 17, Step A, but use ethyl monofluorothiolacetate instead of S—ethyl-trifluoromethylthio-acetate. |
| (27.) | H$_2$CFCH(OH) | H | As in Example 17, Step B, but substitute product No. 26, Table I, Example 14, and use sodium borohydride as reductant. |
| (28.) | N$_3$CH$_2$CH(OH) | H | As in Example 5, but use azidoacetaldehyde instead of acetaldehyde. |
| (29.) | PNBOCCH$_2$(=O) | H | As in Example 5 but substituted p-nitrobenzyl bromoacetate for acetaldehyde. |
| (30.) | MeOCH$_2$C(=O)— | H | As in Example 17, Step A, but substituted N—methoxyacetyl imidazole. |
| (31.) | MeOCH$_2$CH(OH) | H | Obtained by employing the procedure of Example 17, Step B, on compound No. 30, Table I, Example 14. |
| (32.) | CF$_2$CHCH(=O) | H | As in Example 17, Step A, but substitute ethyl difluoro-thiolacetate. |
| (33.) | CF$_2$CHCH(OH) | H | Obtained from No. 32, above, using the procedure of Example 17, Step B, but substituting sodium borohydride as the reducing agent. |

TABLE I-continued

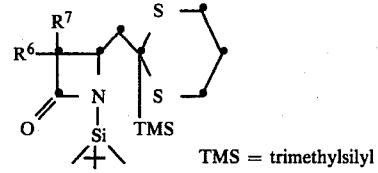

TMS = trimethylsilyl

| Compound | R$^6$ | R$^7$ | Remarks |
|---|---|---|---|
| (34.) | PNBOCOCH$_2$(=O) | CH$_3$ | Obtained from No. 3, Table I, Example 18 with p-nitrobenzyl chloroformate and 4-dimethylaminepyridine in methylenechloride. |
| (35.) | PNBOCOCH$_2$CH$_2$(=O) | H | Obtained from No. 16 Table I, Example 18, by reaction with p-nitrobenzyl chloroformate and triethylamine in methylene chloride. |
| (36.) | PNBOCOCH$_2$CH$_2$(=O) | CH$_3$ | Obtained from No. 24 Table I, Example 18 as described for the preceeding compound No. 35. |
| (37.) | HOCH$_2$ | H | As in Example 5, but use excess formaldehyde instead of acetaldehyde. |
| (38.) | PNBOCOCH$_2$(=O) | H | Obtained from compound 36, above, and p-nitrobenzyl-chloroformate in methylene chloride containing 4-dimethylaminopyridine. |

EXAMPLE 19

Following the foregoing Examples and text, particularly Example 13, the representative intermediates of the present invention are obtained when the indicated substitution from Example 18 is made into the scheme of Example 13.

TABLE II

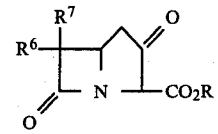

R = PNB (p-nitrobenzyl)

| Compound | R$^6$ | R$^7$ | Remarks |
|---|---|---|---|
| (1.) | (CH$_3$)$_2$CH | H | |
| (2.) | CH$_3$ | H | |
| (3.) | PNBOCOCH$_2$(=O) | CH$_3$ | The primary alcohol, No. 3 Table I, Example 18 is protected as shown by reacting with an equivalent amount of ClCO$_2$PNB in the presence of DMAP (dimethylaminopropane) in methylene chloride. |

TABLE II-continued

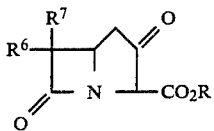

R = PNB (p-nitrobenzyl)

| Compound | $R^6$ | $R^7$ | Remarks |
|---|---|---|---|
| (4.) | $\phi CH_2\underset{\underset{OH}{\mid}}{C}H$ | H | |
| | | $\phi$ = phenyl | |
| (5.) | $CH_3\underset{\underset{OH}{\mid}}{C}H$ | $CH_3$ | |
| (6.) | $\phi CH_2$ | H | |
| (7.) | $CH_3\underset{\underset{OH}{\mid}}{C}H$ | $\phi CH_2$ | |
| (8.) | $CH_3\underset{\underset{N_3}{\mid}}{C}H$ | H | |
| (9.) | $CH_3\underset{\underset{NHCO_2PNB}{\mid}}{C}H$ | H | |
| (10.) | $(CH_3)_2CH\underset{\underset{OH}{\mid}}{C}H$ | H | |
| (11.) | $(CH_3)_2CHCH_2CH_2\underset{\underset{OH}{\mid}}{C}H$ | H | |
| (12.) | cyclopropyl-$\underset{\underset{OH}{\mid}}{C}H$ | H | |
| (13.) | $CF_3\underset{\underset{OH}{\mid}}{C}H$ | $CH_3$ | |
| (14.) | $HOCH_2-\underset{\underset{OH}{\mid}}{C}H-$ | H | |
| (15.) | $PNBOCOCH_2CH_2$ (C=O) | H | Protected as described for No. 3, Table II, Example 19. |
| (16.) | $CH_3CH_2CH_2\underset{\underset{OH}{\mid}}{C}H$ | H | |
| (17.) | $CH_3CH_2\underset{\underset{OH}{\mid}}{C}H$ | H | |
| (18.) | $FCH_2\underset{\underset{OH}{\mid}}{C}H$ | H | |
| (19.) | cyclopropyl-$CH_2\underset{\underset{OH}{\mid}}{C}H$ | H | |
| (20.) | $CH_3CH_2$ | H | |
| (21.) | $CH_3$ | $CH_3$ | |
| (22.) | cyclopropyl-$CH_2$ | H | |
| (23.) | $PNBOCOCH_2CH_2$ (C=O) | $CH_3$ | Protected as described for No. 3, Table II, Example 18. |
| (24.) | cyclopentyl-OH | H | |
| (25.) | $N_3CH_2\underset{\underset{OH}{\mid}}{C}H$ | H | |
| (25a.) | $ClCH_2\underset{\underset{OH}{\mid}}{C}H-$ | H | |
| (25b.) | $ClCH_2\underset{\underset{OH}{\mid}}{C}H-$ | $CH_3$ | |
| (26.) | $PNBOCCH_2$ (C=O) | H | |
| (27.) | $MeOCH_2\underset{\underset{OH}{\mid}}{C}H$ | H | |
| (28.) | $CF_2\underset{\underset{OH}{\mid}}{C}H$ | H | |
| (29.) | $PNBOCOCH_2$ (C=O) | H | |

EXAMPLE 20

Following the foregoing Examples and text, the following compounds are prepared in representative demonstration of the disclosed process. In the following Table, the resulting compounds are taken from starting materials which are made available by the foregoing text and examples—particularly Table II of Example 19. The column labelled "Remarks and Reagents" annotates the established procedure where necessary to obtain the indicated compound. In most instances the compounds are deblocked according to the procedure described in Example 16. However, when the $SR^8$ side chain does not contain a basic function, the final product I is more conveniently isolated as the sodium salt (M=Na); which result is facilitated by conducting the deblocking in a slight excess of $NaHCO_3$. In any event, when either $R^6$ or $R^7$ bears a basic group, the final product I is most conveniently isolated as the free acid (M=H), rather than the sodium salt. It should be noted that compounds designated as "free acids" in reality are isolated as inner salts as a consequence of their zwitterionic nature.

TABLE III $$\text{structure with } R^6, R^7 \text{ on β-lactam, } SR^8 \text{ on pyrroline, COOM} \quad M = H, Na$$

| Compound | $R^6$ | $R^7$ | $R^8$ | Remarks, Reagents |
|---|---|---|---|---|
| (1.) | $(CH_3)_2CH$ | H | $\phi$ | As in Example 15, but substitute $HS\phi$ for $HSCH_2CH_2NHCO_2PNB$. Deblock as described in Example 16 and isolate product as Na salt. M = Na. |
| (2.) | $CH_3$ | H | $CH_2\phi$ | $HSCH_2\phi$; M = Na |
| (3.) | $HOCH_2$ | $CH_3$ | $CH_2CH_2CH_2NH_2$ | $HSCH_2CH_2CH_2NHCO_2PNB$; M = H. |
| (4.) | $\phi CH_2CH(OH)$ | H | $CH_2C(CH_3)_2NH_2$ | $HSCH_2C(CH_3)_2NHCO_2PNB$; M = H. |
| (5.) | $CH_3CH(OH)$ | $CH_3$ | $CH_2CH_2NH_2$ | M = H |
| (6.) | $CH_3CH(OH)$ | $CH_3CH(OH)$ | $CH_2CH_2NH_2$ | M = H |
| (7.) | $CH_3CH(OH)$ | $\phi CH_2$ | $CH_2CH_2N(CH_3)_2$ | $HSCH_2CH_2N(CH_3)_2$; M = H |
| (8.) | $CH_3CH(NH_2)$ | H | $CH_2CH_2NH_2$ | M = H |
| (9.) | $(CH_3)_2CH\text{CH(OH)}$ | H | $CH_2$-(imidazol-2-yl) | $HSCH_2$-(imidazol-2-yl); M = Na |
| (10.) | $(CH_3)_2CHCH_2CH(OH)$ | H | 3-pyridyl | HS-(3-pyridyl); M = H |
| (11.) | cyclopropyl-CH(OH) | H | $CH_2$-(2-pyridyl) | $HSCH_2$-(2-pyridyl); M = H |
| (12.) | $CF_3CH(OH)$ | H | $CH_2CH_2NH_2$ | M = H |
| (13.) | $HOCH_2CH(OH)$ | H | $CH_2CH_2NH_2$ | M = H |
| (14.) | $HOCH_2CH_2$ | H | $CH_2CH_2$-N(piperazinyl)$NCH_3$ | $HSCH_2CH_2$-N(piperazinyl)$NCH_3$; M = H |
| (14a.) | $CH_2=CH-CH(OH)$ | H | $CH_2CH_2NH_2$ | M = H |
| (15.) | $CH_3CH_2CH_2CH(OH)$ | H | $CH_2$-(2-pyridyl) | $HSCH_2$-(2-pyridyl); M = H |

TABLE III-continued

| | | | | |
|---|---|---|---|---|
| (16.) | CH₃CH₂CH(OH)— | H | 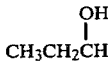 o-(CH₂NH₂)-phenyl | 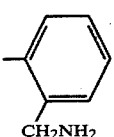 HS-phenyl-o-CH₂NHCO₂PNB; M = H |
| (17.) | FCH₂CH(OH)— | H | CH₂CH₂NH₂ | |
| (18.) | cyclopropyl-CH₂CH(OH)— | H | CH₂CH₂CO₂H | HSCH₂CH₂CO₂PNB; Product isolated as disodium salt. |
| (19.) | CH₃CH₂ | H | CH₂CH₂NH₂ | |
| (20.) | CH₃ | CH₃ | 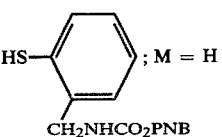 1-methyl-tetrazol-5-yl | 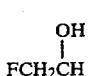 HS-(1-methyl-tetrazol-5-yl); M = Na |
| (21.) | cyclopropyl-CH₂ | H | CH₂CH₂OH | HSCH₂CH₂OH; M = Na |
| (22.) | HOCH₂CH₂ | CH₃ | CH₂CH₂CH₂CH₂NH₂ | HSCH₂CH₂CH₂CH₂NHO₂PNB; M = H |
| (23.) | 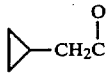 3-hydroxycyclopentyl | H | CH₂C(CH₃)₂CH₂NH₂ | CH₂C(CH₃)₂CH₂NHCO₂PNB; M = H |
| (24.) | 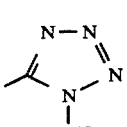 3-hydroxycyclopentyl | H | CH₂CH₂NH₂ | M = Na |
| (25.) | 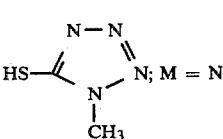 2-methyl-hydroxycyclopentyl | H | CH₂CH₂NH₂ | M = Na |
| (26.) | CH₃CH(OH)— | H | —SCH₂CH₂CH₃ | HSCH₂CH₂CH₃; M = Na |
| (27.) | " | H | —SCH₂CH₂OH | HSCH₂CH₂OH; M = Na |
| (28.) | " | H | —SCH₂CH₂NH₂ | HSCH₂CH₂NHCO₂PNB; M = H |
| (29.) | " | H | —SCH₂CH₂NHC(O)CH₃ | HSCH₂CH₂NHC(O)CH₃; M = Na |
| (30.) | " | H | —SCH(CH₃)CH₂NH₂ | HSCH(CH₃)CH₂NHCO₂PNB; M = H |
| (31.) | " | H | —SC(CH₃)₂CH₂NH₂ | HSC(CH₃)₂CH₂NHCO₂PNB; M = H |
| (32.) | " | H | —SCH₂CH(CH₃)NH₂ | HSCH₂CH(CH₃)NHCO₂PNB; M = H |
| (33.) | " | H | —SCH₂C(CH₃)₂NH₂ | HSCH₂C(CH₃)₂NHCO₂PNB; M = H |
| (34.) | " | H | —SCH₂CH(CH₃)CH₂NH₂ | HSCH₂CH(CH₃)CH₂NHCO₂PNB; M = H |

TABLE III-continued
| | | | | |
|---|---|---|---|---|
| (35.) | " | H | 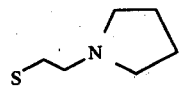 | 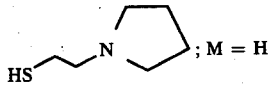 ; M = H |
| (36.) | " | H | S⌒N(CH₃)₂ | HS⌒N(CH₃)₂; M = H |
| (37.) | " | H | 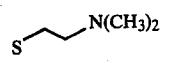 | 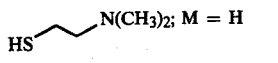 ; M = H |
| (38.) | " | H | 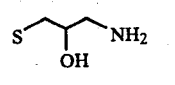 | 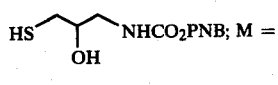 ; M = H |
| (39.) | " | H | 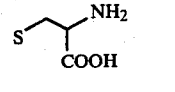 | 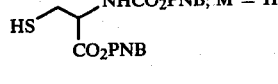 ; M = H |
| (40.) | " | H | 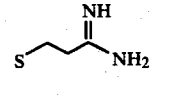 | 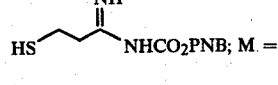 ; M = H |
| (41.) | " | H | S⌒NHφ | M = H |
| (42.) | " | H | 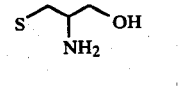 | 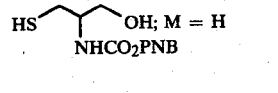 M = H |
| (43.) | " | H | Sφ | M = Na |
| (44.) | " | H |  |  M = H |
| (45.) | " | H | 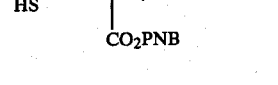 | 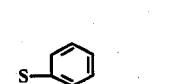 ; M = H |
| (46.) | " | H | 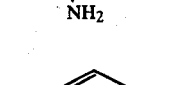 | M = Na |
| (47.) | " | H | 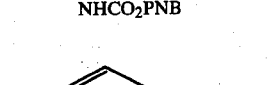 | M = Na |
| (48.) | " | H | 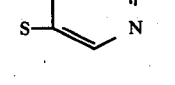 | M = H |
| (49.) | " | H | 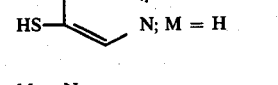 | M = H |
| (50.) | " | H | 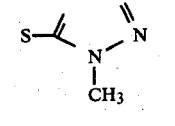 | 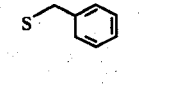 ; M = H |

TABLE III-continued

| | | | | |
|---|---|---|---|---|
| (51.) | " | H | [structure: S-CH=N-CH=CH-NH ring] | M = Na |
| (52.) | " | H | [structure: S-C(=N)-S-C=C with NH₂] | [structure: HS-C=C-S-C(=N)-NHCO₂PNB] M = H. |
| (53.) | " | H | [structure: S-CH₂-N(piperazine)NCH₃] | M = H |
| (54.) | " | H | [structure: S-(piperidine)-NCH₃] | M = H |
| (55.) | " | H | [structure: S-CH₂-C(=N)-N-CH₂ ring, NH] | [structure: HS-CH₂-CH(N-CH₂ ring)-CO₂PNB] ; M = H |
| (56.) | " | H | [structure: S-CH₂CH₂-O-CH₂CH₂-NH₂] | [structure: HS-CH₂CH₂-O-CH₂CH₂-NHCO₂PNB] M = H |
| (57.) | " | H | [structure: S-CH₂CH₂-N(CH₃)-CH₂CH₂-NH₂] | [structure: HS-CH₂CH₂-N(CH₃)-CH₂CH₂-NHCO₂PNB]; M = H |

| Compounds | |
|---|---|
| 58–89 | Compounds 58–89 correspond sequentially to compounds 26–57, above, except that the value for $R^6$ is taken as $CH_3CH_2$ rather than the $CH_3C(OH)H$ of Compounds 26–57. |
| 90–121 | Compounds 90–121 correspond sequentially to compounds 26–57, above, except that the value for $R^6$ is taken as $Cl_2CHCH(OH)$ rather than the $CH_3C(OH)H$ of Compounds 26–57. |
| 122–153 | Compounds 122–153 corespond sequentially to compounds 26–57, above, except that the value for $R^6$ is taken as $CF_3CH(OH)$ rather than the $CH_3(OH)H$ of Compounds 26–57. |
| 154–185 | Compounds 154–185 correspond sequentially to compounds 26–57, above, except that the value for $R^6$ is taken as $HOCH_2CH(OH)$ rather than the $CH_3C(OH)H$ of Compounds 26–57. |
| 186–217 | Compounds 186–217 correspond sequentially to compounds 26–57, above, except that the value for $R^6$ is taken as $ClCH_2CH(OH)$ rather than the $CH_3C(OH)H$ of Compounds 26–57. |
| 218–249 | Compounds 218–249 correspond sequentially to compounds 26–57, above, except that the value for $R^6$ is taken as $CH_3CH_2CH(OH)$ rather than the $CH_3C(OH)H$ of Compounds 26–57. |
| 250–281 | Compounds 250–281 correspond sequentially to compounds 26–57, above, except that the vlue for $R^6$ is taken as cyclopropyl-CH(OH) rather than the $CH_3C(OH)H$ of Compounds 26–57. |
| 282–313 | Compounds 282–313 correspond sequentially to compounds 26–57, above, except that the value for $R^6$ is taken as $H_2NCH_2CH(OH)$ rather than the $CH_3C(OH)H$ of Compounds 26–57. |
| 314–345 | Compounds 314–345 correspond sequentially to compounds |

| | |
|---|---|
| | 26–57, above, except that the value for R⁶ is taken as CF₂HC(OH)— rather than the CH₃C(OH)H of Compounds 26–57. |
| 346–377 | Compounds 346–377 correspond sequentially to compounds 26–57, above, except that the value for R⁶ is taken as HOCH₂ rather than the CH₃C(OH)H of Compounds 26–57. |
| 378–409 | Compounds 378–409 correspond sequentially to compounds 26–57, above, except that the value for R⁶ is taken as HO₂CCH₂ rather than the CH₃C(OH)H of Compounds 26–57. |
| 410–441 | Compounds 410–441 correspond sequentially to compounds 26–57, above, except that the value for R⁶ is taken as CH₃OCH₂CH(OH) rather than the CH₃C(OH)H of Compounds 26–57. |
| 442–473 | Compounds 442–473 correspond sequentially to compounds 26–57, above, except that the value for R⁶ is taken as (CH₃)₃CCH₂CH(OH) rather than the CH₃C(OH)H of Compounds 26–57. |

φ = phenyl

What is claimed is:

1. A process for preparing

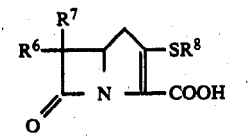

wherein: $R^6$, $R^7$ and $R^8$ are independently selected from the group consisting of: hydrogen; substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the aliphatic portion has 1–6 carbon atoms; wherein the substituent or substituents relative to the above-named radicals are selected from the group consisting of:

chloro, bromo, fluoro, —OH, —OR¹, —OCNR¹R², —CNR¹R²,
(with C=O)

NR¹R², —NH₂, —NHR¹, —C(=NR¹)(NR¹R²), —SO₂NR¹R²,

—NHCNR¹R², —R²NCR¹, —CO₂H, —CO₂R¹, —CR¹,
(with C=O groups)

—OCR¹, —SH, —SR¹, —SR¹ (with two =O), —CN, and —N₃ wherein, relative to the above listed substituents on $R^8$, $R^6$ and $R^7$, the groups $R^1$ and $R^2$ are independently selected from: hydrogen, alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the aliphatic portion has 1–6 carbon atoms; when $R^6/R^7$ is hydrogen, then $R^7/R^6$ is not $$\overset{OH}{\underset{}{\wedge}}$$

when $R^8$ is CH₂CH₂NH₂; which process comprises the steps of oxidizing:

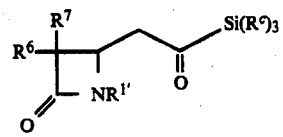

to form:

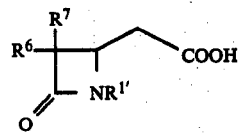

wherein $R^{1'}$ is hydrogen or a triorganosilyl or 3,4-dimethoxybenzyl protecting group; and $R^c$ is independently selected from alkyl having 1–6 carbon atoms and phenyl; followed by treating with 1,1'-carbonyldimidazole followed by R²'O₂CCH₂CO₂)₂Mg to yield:

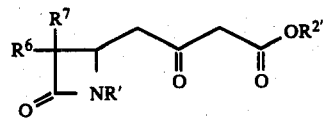

wherein $R^{2'}$ is a protecting group selected from p-nitrobenzyl or benzyl; followed by hydrolysis to yield:

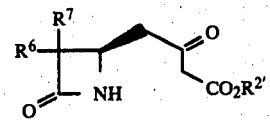

followed by treating with a diazotizing agent selected from p-carboxybenzenesulfonylazide, toluene sulfonylazide, methanesulfonylazide, toluenesulfonylazide, and methanesulfonylazide to yield:

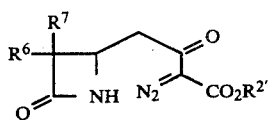

followed by cyclizing in the presence of a catalyst selected from bis(acetylacetonato)Cu (II), CuSO$_4$, Cu powder, $$Rh(OCCH_3)_2, \text{ and } Pd(OCCH_3)_2$$
$$\phantom{Rh(O}\|\phantom{CCH_3)_2, \text{ and } Pd(O}\|$$
$$\phantom{Rh(}O\phantom{CCH_3)_2, \text{ and } Pd(}O$$

to yield:

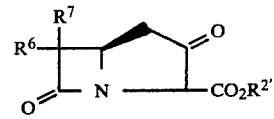

Followed by activating by treating with an acylating agent selected from p-toluenesulfonic acid anhydride, p-nitrophenylsulfonic acid anhydride, 2,4,6-triisopropylphenylsulfonic acid anhydride, methanesulfonic acid anhydride, trifluoromethane sulfonic acid anhydride, diphenyl chlorophosphate, toluenesulfonyl chloride, and p-bromophenylsulfonyl chloride; followed by reacting with HSR$^8$ and deblocking.

* * * * *